United States Patent
Akimoto et al.

(10) Patent No.: US 9,345,394 B2
(45) Date of Patent: May 24, 2016

(54) MEDICAL APPARATUS

(71) Applicant: OLYMPUS CORPORATION, Tokyo (JP)

(72) Inventors: Syunya Akimoto, Kawasaki (JP); Junichi Onishi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1 day.

(21) Appl. No.: 14/245,075

(22) Filed: Apr. 4, 2014

(65) Prior Publication Data

US 2014/0253685 A1 Sep. 11, 2014

Related U.S. Application Data

(63) Continuation of application No. PCT/JP2013/070878, filed on Aug. 1, 2013.

(30) Foreign Application Priority Data

Sep. 7, 2012 (JP) .................................. 2012-197405

(51) Int. Cl.
*A61B 1/05* (2006.01)
*A61B 1/00* (2006.01)
(Continued)

(52) U.S. Cl.
CPC ............... *A61B 1/05* (2013.01); *A61B 1/00009* (2013.01); *A61B 1/07* (2013.01); *A61B 5/0037* (2013.01); *A61B 1/00193* (2013.01); *A61B 1/2676* (2013.01)

(58) Field of Classification Search
CPC .... A61B 1/00193; A61B 5/0037; A61B 1/05; A61B 1/07; A61B 1/2676; A61B 2019/5289; A61B 1/00009; H04N 13/0239; H04N 2005/2255

USPC .......................................................... 348/45
See application file for complete search history.

(56) References Cited

U.S. PATENT DOCUMENTS

2010/0094085 A1* 4/2010 Yamamoto et al. ............ 600/109
2012/0069167 A1* 3/2012 Liu et al. .......................... 348/65

FOREIGN PATENT DOCUMENTS

EP 2 123 216 A1 11/2009
EP 2 123 232 A1 11/2009
(Continued)

OTHER PUBLICATIONS

International Search Report dated Nov. 12, 2013 issued in PCT/JP2013/070878.
(Continued)

*Primary Examiner* — William C Vaughn, Jr.
*Assistant Examiner* — Naod Belai
(74) *Attorney, Agent, or Firm* — Scully, Scott, Murphy & Presser, P.C.

(57) ABSTRACT

A medical apparatus includes: a storage section that stores three-dimensional image information in a subject, the three-dimensional image information being acquired in advance; an image pickup unit that acquires an optical image in the subject; a luminal organ extracting section that extracts image information of a three-dimensional shape of a specific luminal organ in the subject; a position correspondence control section that sets correspondence between two coordinate systems; a feature information acquisition section that acquires feature information in the image information of the extracted three-dimensional shape of the specific luminal organ; an associated image generating section that generates an image in which the feature information is associated with the image information of the three-dimensional shape of the specific luminal organ; a control section that performs control to display a piece of the feature information in the vicinity of the position information of the image pickup unit, etc.

13 Claims, 17 Drawing Sheets

(51) Int. Cl.
   *A61B 1/07*   (2006.01)
   *A61B 5/00*   (2006.01)
   *A61B 1/267*  (2006.01)

(56) References Cited

FOREIGN PATENT DOCUMENTS

| JP | 2004-089483 A | 3/2004 |
|---|---|---|
| JP | 2005-131042 A | 5/2005 |
| JP | 2005-131046 A | 5/2005 |
| JP | 2007-007041 A | 1/2007 |
| JP | 2009-056239 A | 3/2009 |
| JP | 2012-165838 A | 9/2012 |
| WO | WO 2012/108085 A1 | 8/2012 |

OTHER PUBLICATIONS

Extended Supplementary European Search Report dated Jan. 21, 2016 from related European Application No. 13 83 5529.2.

* cited by examiner

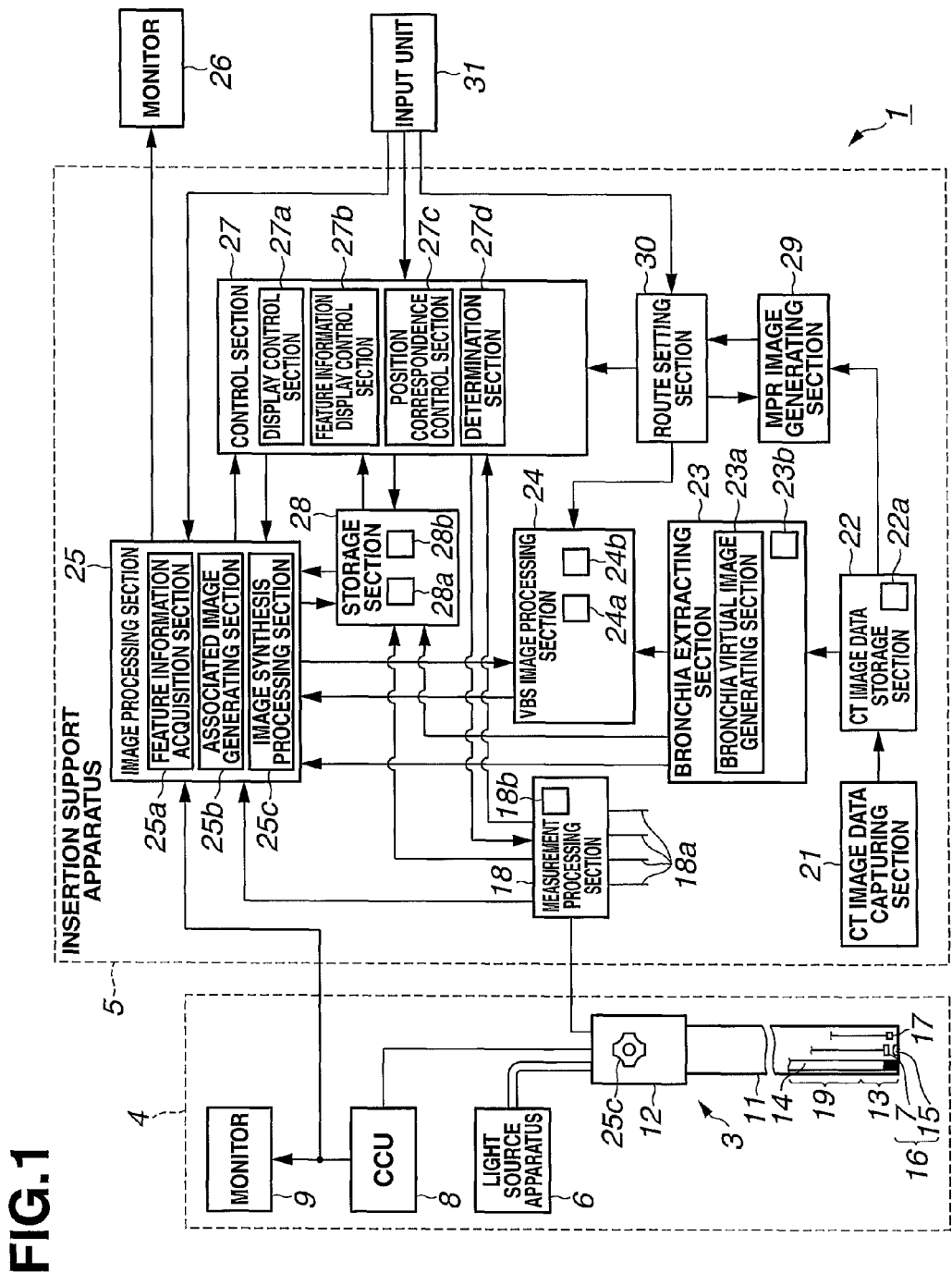

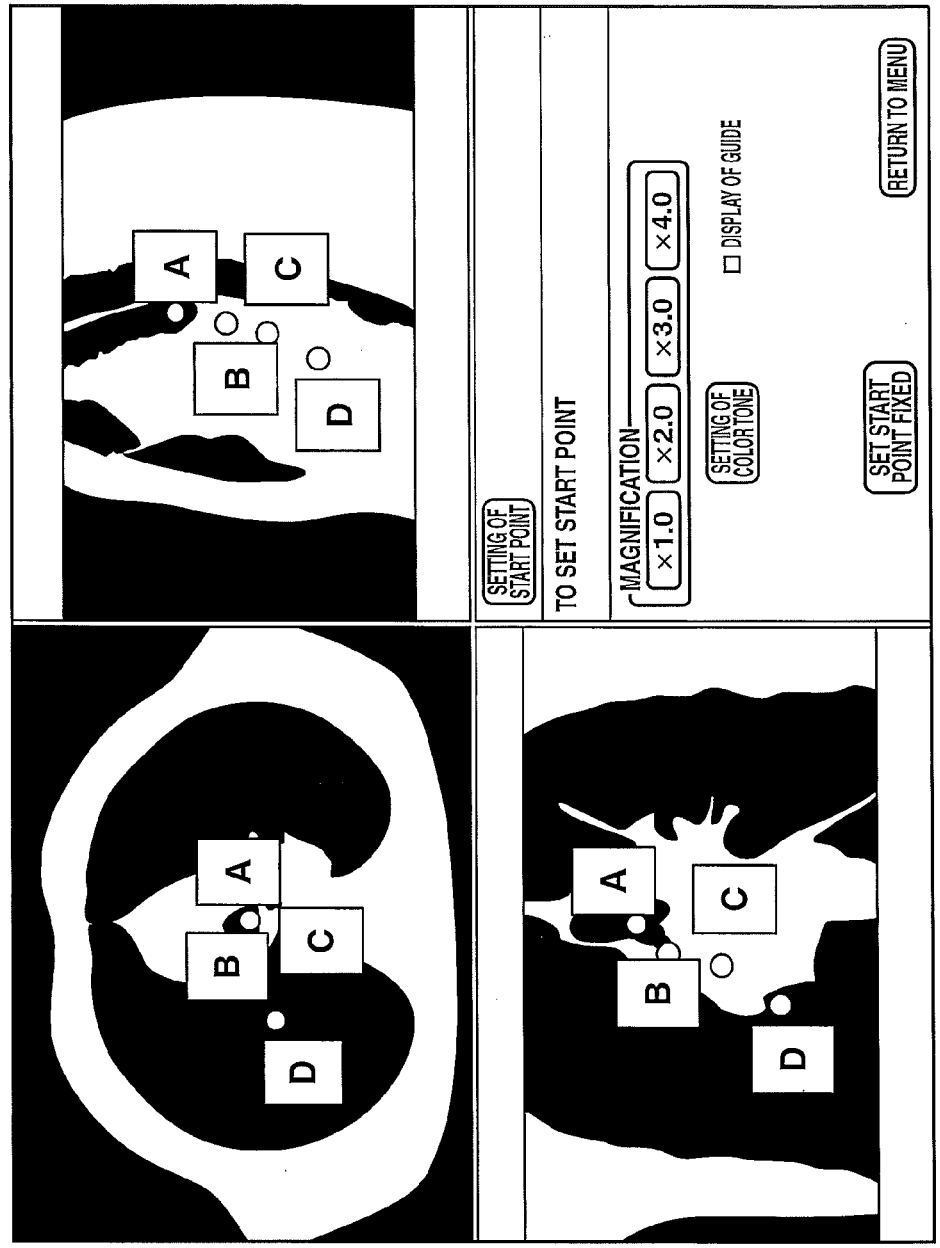
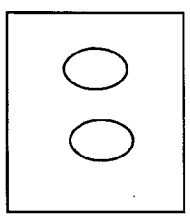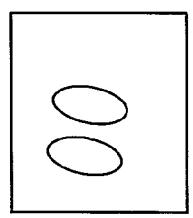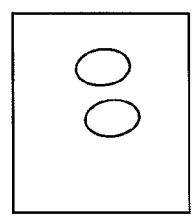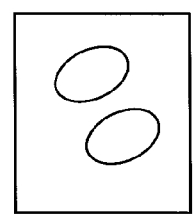
FIG.17

MEDICAL APPARATUS

CROSS REFERENCE TO RELATED APPLICATION

This application is a continuation application of PCT/JP2013/070878 filed on Aug. 1, 2013 and claims benefit of Japanese Application No. 2012-197405 filed in Japan on Sep. 7, 2012, the entire contents of which are incorporated herein by this reference.

BACKGROUND OF THE INVENTION

1. Field of the Invention

The present invention relates to a medical apparatus for picking up an image inside a subject.

2. Description of the Related Art

An endoscope, as a medical apparatus, for insertion into a subject and with image pickup means provided at a distal end portion has been widely used in a medical field and other fields.

Further, in order to make it possible to smoothly perform an examination with an endoscope inserted into a luminal organ of the subject or a treatment by a treatment instrument in accordance with an examination result, or the like, a medical apparatus in combination with information of a CT apparatus and the like has been proposed.

For example, a surgery support apparatus disclosed in Japanese Patent Laid-Open Publication No. 2007-7041, as a first conventional example, comprises a three-dimensional position detecting device for detecting a location of an endoscope sequentially, image creation means for creating a surgery support image to be superposed on an image by the endoscope and coordinate integration means for integrating coordinates of the three-dimensional position detecting device and image coordinates which the image creation means has.

The image creation means creates the surgery support image to be superposed on the image by the endoscope using three-dimensional volume image data of a subject picked up by an MRI, etc. By the coordinate integration means, even when a position and a direction of the endoscope are changed, it is configured that the surgery support image can be displayed as being superposed in consistency with the direction of the endoscope with a relative position thereto maintained.

Further, Japanese Patent Laid-Open Publication No. 2005-131042, as a second conventional example, discloses an insertion support system for supporting an endoscope inserted into bronchia by creating a virtual endoscopic image at a plurality of bifurcation points of the bronchia.

SUMMARY OF THE INVENTION

A medical apparatus according to an aspect of the present invention includes: a storage section configured to store three-dimensional image information in a subject, the three-dimensional image information being acquired in advance; an image pickup unit that includes an objective lens and acquires an optical image in the subject; a luminal organ extracting section configured to extract image information of a three-dimensional shape of a specific luminal organ in the subject from the three-dimensional image information; a position correspondence control section that sets correspondence between position information in the image information of the three-dimensional shape of the specific luminal organ in a first coordinate system and position information of the image pickup unit in a second coordinate system; a feature information acquisition section configured to acquire feature information in the image information of the three-dimensional shape of the specific luminal organ extracted by the luminal organ extracting section in a region where the image pickup unit is inserted based on the position information of the image pickup unit inserted into the specific luminal organ; an associated image generating section configured to generate an image in which the feature information is associated with the image information of the three-dimensional shape of the specific luminal organ; a determination section that determines whether or not position information of the image pickup unit in the first coordinate system, which is set to have correspondence and subjected to position estimation by the position correspondence control section, is consistent with a position of the image pickup unit in the specific luminal organ within a predetermined condition; and a control section configured to perform control to display, on a display section, a piece of the feature information in a vicinity of the position information of the image pickup unit in the specific luminal organ, when it is determined that the position information of the image pickup unit in the first coordinate system is not consistent within the predetermined condition by the determination section.

BRIEF DESCRIPTION OF THE DRAWINGS

FIG. 1 is a diagram showing an entire configuration of a medical apparatus according to a first embodiment of the present invention;

FIG. 17 is a diagram showing display examples of an associated images in which the position of the image pickup unit and also the virtual endoscopic image are displayed on the CT tomographic image in a ninth modified example of the second embodiment.

DETAILED DESCRIPTION OF THE PREFERRED EMBODIMENTS

Figure 2A:
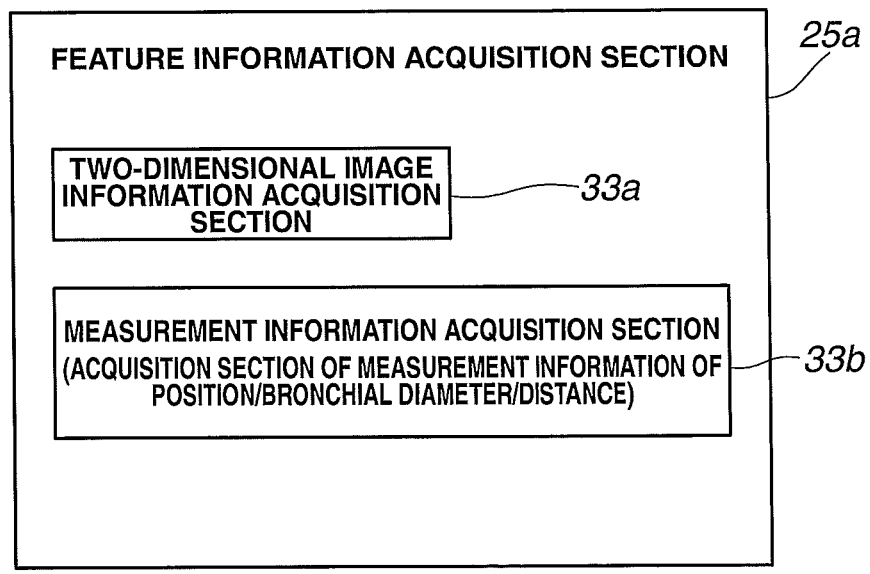
FIG. 2A is a block diagram showing a configuration of a feature information acquisition section.

Hereinafter, embodiments of the present invention will be described referring to the drawings.

(First Embodiment)

As shown in FIG. 1, a medical apparatus 1 according to the first embodiment of the present invention is configured to mainly comprise an endoscope apparatus 4 including an endoscope 3 to be inserted into bronchia 2 (see FIGS. 2 and 7, a part of the bronchia is shown by the dotted line in FIG. 2) as a specific luminal organ of a patient as a subject to be examined, and an insertion support apparatus 5 to be used with the endoscope apparatus 4 for performing an insertion support of the endoscope.

The endoscope apparatus 4 includes the endoscope 3, a light source apparatus 6 for supplying illumination light to the endoscope 3, a camera control unit (abbreviated as CCU) 8 as a signal processing unit for performing signal processing with respect to an image pickup device 7 which is mounted in the endoscope 3 and constitutes image pickup means, and a monitor 9 for displaying an endoscopic image generated by the CCU 8.

The endoscope 3 includes an elongated insertion portion 11 having flexibility, an operation portion 12 provided at a rear end of the insertion portion 11, and at a distal end portion 13 of the insertion portion 11, an illumination window and an observation window are provided. A light guide 14 for transmitting the illumination light is inserted into the insertion portion 11 and the operation portion 12, and a light entering end of the light guide 14 is connected to the light source apparatus and the illumination light generated by a light source lamp or an LED, which is not shown, in the light source apparatus 6 is incident on the light entering end. The illumination light transmitted by the light guide 14 is emitted forward from an emitting end (a distal end face) attached to the illumination window.

Further, an objective lens 15 is attached to the observation window and the image pickup device 7 such as a CCD is arranged at an image forming position and an image pickup unit 16 is formed by the objective lens 15 and the image pickup device 7, as image pickup means for picking up an image inside the bronchia 2 as the specific luminal organ into which the insertion portion 11 is inserted.

The image pickup device 7 is connected to the CCU 8 through a signal line inserted through the insertion portion 11 and the operation portion 12. The CCU 8 generates, by an image signal generating circuit provided therein and not shown, an image signal of a picked-up image corresponding to an optical image formed on an image pickup surface of the image pickup device 7, and outputs the image signal to the monitor 9. The monitor 9 displays an image (moving image) according to the image signal as the endoscopic image (also referred to as the picked-up image).

Further, inside the distal end portion 13, a position sensor 17 is provided in the vicinity of the image pickup device 7. Furthermore, a measurement processing apparatus or measurement processing section 18 which performs processing of measuring (detecting) a three-dimensional position (also referred to simply as "position") of the position sensor 17 is provided at a predetermined position outside of the endoscope 3 and the subject.

The measurement processing section 18 measures the position of the position sensor 17 and the position can be approximated as a position of the distal end portion 13 or (the image pickup device 7 of) the image pickup unit 16.

The measurement processing section 18 has a function of a position information generating section 18b which generates information of a position at which the image pickup unit 16, that constitutes image pickup means to be inserted into the bronchia 2 as the specific luminal organ, is located using the position sensor 17.

As a position detecting method, a method using magnetism can be utilized. For example, an alternating magnetic field generated by an antenna 18a connected to the measurement processing section 18 is sensed by the position sensor 17 constituted by a coil, and an amplitude and a phase of a signal detected by the position sensor 17 are detected by the measurement processing section 18 (including an amplitude detecting circuit and a phase detecting circuit), thereby a distance from an antenna 18a to the position sensor 17 is measured. The measurement processing section 18 specifies a three-dimensional position of the position sensor 17 by providing a plurality of, three or more, antennas 18a at known different positions.

Besides, it may be configured such that an alternating signal is applied to the coil constituting the position sensor 17 to generate an alternating magnetic field in the periphery thereof and the alternating magnetic field is sensed by the antennas 18a so that the location of the position sensor 17 is detected. Although the magnetic position detecting apparatus using the coil has been described as an example, the configuration of the position sensor 17 and the measurement processing section 18 is not limited to the above-described case. For example, it may be configured such that a plurality of coils are arranged for position detection at predetermined intervals along a longitudinal direction of the insertion portion 11 and a shape of the insertion portion 11 is estimated from the positions of the plurality of coils, so that positions of the distal end portion 13, etc. can be detected.

It is noted that at the insertion portion 11 of the endoscope 3, a bending portion 19 that is bendable is provided at a rear end of the distal end portion 13 and a surgeon can bend the bending portion 19 in arbitrary directions of up/down and right/left by performing an operation to rotate bending operation knobs 25c provided at the operation portion 12.

The insertion support apparatus 5 includes a CT image data capturing section 21 that captures CT image data as three-dimensional image information of a patient which has been generated by a known CT apparatus with respect to the patient who undergoes an examination by the endoscope 3 through a portable storage medium such as a DVD, a Blu-ray Disc and a flash memory, and a CT image data storage section 22 that stores the CT image data captured by the CT image data capturing section 21.

Besides, the CT image data storage section 22 may store the CT image data (of the patient as a subject) generated by the CT apparatus through a communication line, the internet, etc. The CT image data storage section 22 is constituted by a hard disc unit, a flash memory, a DVD, or the like.

Further, the CT image data storage section 22 includes an associated information storage section 22*a* that stores associated information which associates the CT image data with three-dimensional position data using a first coordinate system to be associated with the CT image data.

Furthermore, the insertion support apparatus 5 includes a bronchia extracting section 23, as a luminal organ extracting section or a luminal organ extracting circuit, that extracts three-dimensional image data of the bronchia 2 as the specified luminal organ from the CT image data in the CT image data storage section 22.

The bronchia extracting section 23 generates image information (image data) of a three-dimensional shape which represents a hollow shape of the bronchia 2 from the extracted three-dimensional image data (more specifically, three-dimensional volume data) of the bronchia 2. That is, the bronchia extracting section 23 includes a bronchia virtual image generating section 23*a* having a bronchia virtual image generating circuit that generates a bronchia shape virtual image as a virtual image of the bronchia shape in a hollow three-dimensional shape from the extracted three-dimensional image data of the bronchia 2.

Further, the bronchia extracting section 23, when extracting the image data of the three-dimensional shape of the bronchia 2, makes extraction of the three-dimensional image data to be associated with the three-dimensional position data in the first coordinate system. Furthermore, the bronchia extracting section 23 includes an associated information storage section 23*b*, constituted by a memory and the like, that stores associated information which associates the image data of the three-dimensional shape of the bronchia 2 (i.e. bronchia shape virtual image data) with the three-dimensional position data.

Further, the insertion support apparatus 5 includes a VBS image processing section 24 that performs image processing for generating a virtual endoscopic image (which is referred to as "VBS image") when picking up an image inside the bronchia 2 based on the information of the position where the image pickup unit 16 is located.

The VBS image processing section 24 comprises a VBS image generating section 24*a* that generates a VBS image, and a VBS image storage section 24*b* that stores the generated VBS image. Besides, it may be configured that the VBS image storage section 24*b* is provided outside of the VBS image processing section 24.

Further, the insertion support apparatus 5 includes an image processing section 25, constituted by an image processing circuit, which comprises a feature information acquisition section 25*a* that performs image processing of acquiring feature information in the image information of the three-dimensional shape of the bronchia 2 as the specific luminal organ which is extracted by the bronchia extracting section 23, and an associated image generating section 25*b* that generates a feature information associated image as an image with the feature information associated with the image information of the three-dimensional shape of the bronchia 2.

The feature information acquisition section 25*a* includes, as shown in FIG. 2A, a two-dimensional image information acquisition section 33*a* that acquires two-dimensional image information regarding branches in the bronchia 2 and a measurement information acquisition section 33*b* that mainly acquires measurement information regarding the branches in the bronchia 2.

The two-dimensional image information acquisition section 33*a*, by acquiring the two-dimensional image information regarding the branches in the bronchia 2, makes use thereof in generating the VBS image as a virtual endoscopic image of a branch portion branching in the bronchia 2 based on the acquired information. It is noted that the VBS image processing section 24 generates the VBS images including a branch portion and an un-branched portion. Therefore, the two-dimensional image information acquisition section 33*a* may be provided in the VBS image processing section 24.

Further, in FIG. 1, the image processing section 25 and the VBS image processing section 24 are shown as separate units, but it may be configured, for example, that the image processing section 25 includes the VBS image generating section 24*a* in the VBS image processing section 24.

The measurement information acquisition section 33*b* includes a position/bronchial diameter/distance measurement information acquisition section that acquires measurement information regarding the branches in the bronchia 2, more specifically, measurement information of positions (a position of the image pickup unit 16 in the second coordinate system and a position in the first coordinate system corresponding to the position of the image pickup unit), a bronchial diameter and a distance to a predetermined position in the bronchia 2.

Besides, it is not limited to a case where the measurement information acquisition section 33*b* acquires the three pieces of measurement information of the position, the bronchial diameter and the distance, it may be configured that the measurement information acquisition section 33*b* acquires two or at least one of these pieces of measurement information. Further, it is not limited that the feature information acquisition section 25*a* includes both of the two-dimensional image information acquisition section 33*a* and the measurement information acquisition section 33*b*, but it may be configured that the feature information acquisition section 25*a* may include one of these sections. Further, it is not limited to the case where the measurement information acquisition section 33*b* is provided in the feature information acquisition section 25*a* in the image processing section 25, but the measurement information acquisition section 33*b* may be provided in the measurement processing section 18, for example, outside of the image processing section 25 and may be provided as a separate unit from the image processing section 25 and the measurement processing section 18.

The feature information is used as information of the insertion support and forms information which is presented for dealing with a case where position estimation under a predetermined condition results in failure.

Further, the image processing section 25 includes an image synthesis processing section 25*c* that performs image processing of synthesizing the bronchia shape virtual image, the virtual endoscopic image (VBS image) inside the bronchia 2 and the endoscopic image (picked-up image) by the image pickup device 7, etc. The image synthesis processing section 25*c* outputs (an image signal of) a synthesized synthetic image to a monitor 26 as display means, and the synthetic image is displayed on the monitor 26.

Figure 2B:
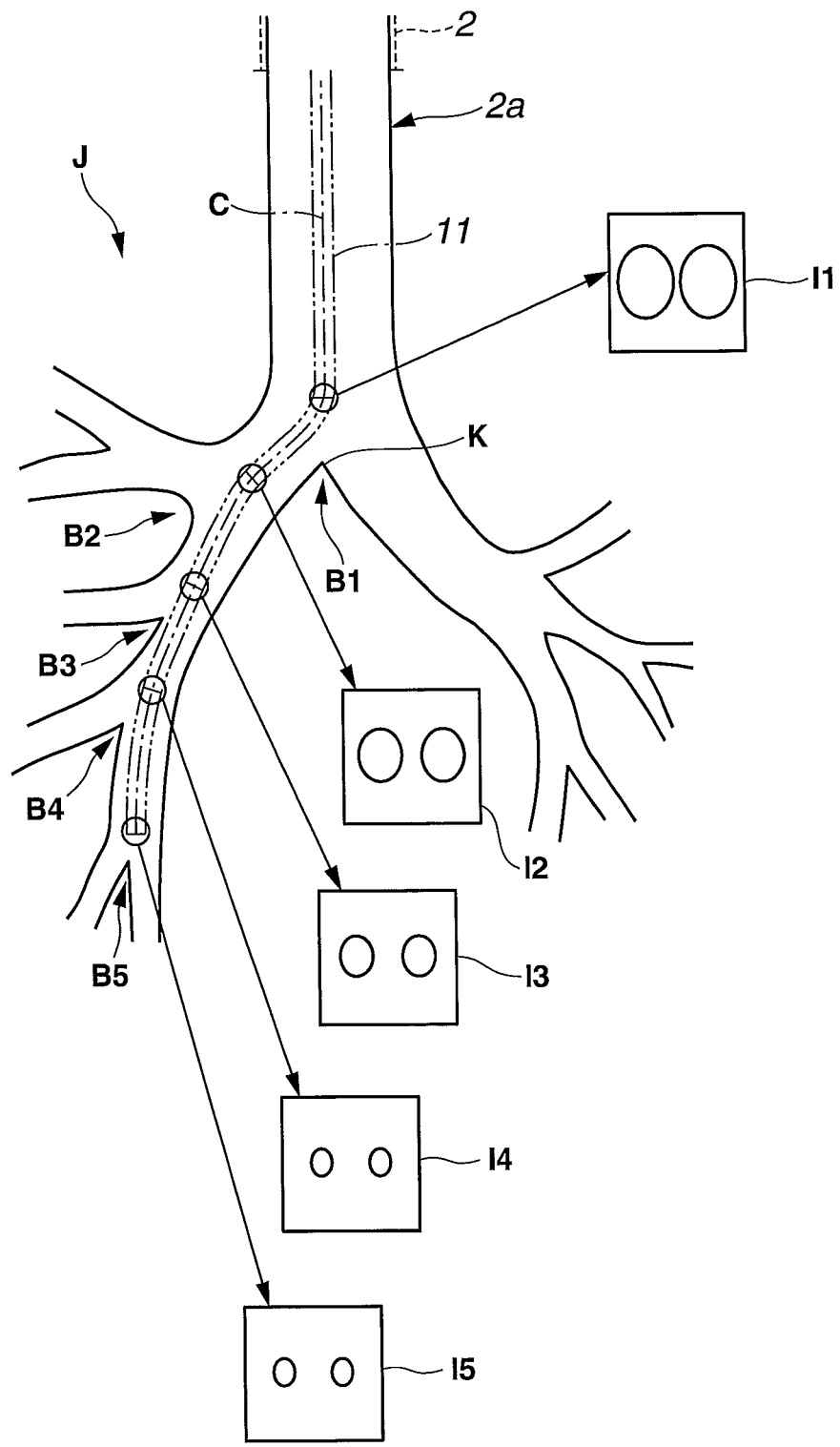
FIG. 2B is a diagram showing a bronchia virtual image and so forth showing a three-dimensional shape of the bronchia.

FIG. 2B shows a bronchia shape virtual image 2*a* generated by the bronchia virtual image generating section 23*a*. It is noted that the bronchia shape virtual image 2*a* is stored in the associated information storage section 23*b* with the image data thereof to be associated with the corresponding three-dimensional position information.

In FIG. 1, the feature information acquisition section 25a is shown to be provided in the image processing section 25, but it may be configured that the feature information acquisition section 25a is provided in the VBS image processing section 24 outside of the image processing section 25, or in the bronchia extracting section 23, or at other positions. In this case, the feature information acquired by the feature information acquisition section 25a is inputted to the image generating section 25b of the image processing section 25.

The image signal generated by the image processing section 25 including the case of the synthetic image is outputted to the monitor 26 as image display means and the image of the image signal is displayed on the monitor 26.

Further, the insertion support apparatus 5 includes a control section 27 constituted by a CPU or the like for controlling image processing and the like by the image processing section 25, a storage section 28 that stores images to be displayed on the monitor 26, position correspondence information indicating correspondence between a position of the coordinate system (the first coordinate system) used in generating the CT image data and also in generating the bronchia shape virtual image 2a, and a position of the coordinate system (the second coordinate system) used in measurement of the position of the image pickup unit 16 by the sensor 17 and the measurement processing section 18.

The control section 27 has a function of an image display control section 27a that performs display control of an image to be displayed on the monitor 26.

Further, the control section 27 includes a feature information (in the vicinity of position information) display control section 27b that controls display of the feature information of the bronchia 2 in the vicinity of the position information of the image pickup unit 16 in the bronchia 2 as the specific luminal organ, on the monitor as the display means. Thus, the monitor 26 displays the feature information of the bronchia 2 in the vicinity of the position information.

Furthermore, in the present embodiment, in order to support an insertion operation of the endoscope 3 smoothly into the bronchia 2 (by the surgeon), position correspondence or position adjustment (registration) is performed between a position (position information) in the first coordinate system for managing the image data of the three-dimensional shape of the bronchia 2, and the position (position information) of the image pickup unit 16 in the second coordinate system at the distal end portion 13 of the insertion portion 11 of the endoscope 3 inserted into the bronchia 2.

The control section 27 has a function of a position correspondence control section 27c that performs control of setting the position correspondence in the coordinate systems.

The position correspondence information set by the position correspondence is stored, for example, in a position correspondence information storage section 28a in the storage section 28.

Further, the control section 27 has a function of a determination section 27d that determines whether or not the position information in the coordinate systems has succeeded in position estimation within a predetermined condition after setting the position correspondence.

Further, the insertion support apparatus 5 includes an MPR image generating section 29 that generates a multiplanar reconstruction image (which is referred to as "MPR image") based on the CT image data stored in the CT image data storage section 22, and a route setting section 30 that generates a route setting screen (or a path setting screen), as a setting screen of a support route (which is referred to simply as "route") or a support path, which includes MPR images generated by the MPR image generating section 29 for setting a route of the endoscope 3 to the bronchia 2.

Further, the medical apparatus 1 includes an input unit 31 constituted by a keyboard and a pointing device and the like for inputting setting information to the route setting section 30. Further, the surgeon is allowed to input parameters or data in performing the image processing from the input unit 31 to the image processing section 25, and to select and instruct a control operation with respect to the control section 27.

Furthermore, when the surgeon performs the route setting, the route setting section 30 sends information of the set route (path) to the VBS image processing section 24, the MPR image generating section 29 and the control section 27. The VBS image processing section 24 and the MPR image generating section 29 respectively generate the VBS image and the MPR image along the route, and the control section 27 performs control of operations of the respective sections.

The feature information acquisition section 25a acquires, as the feature information regarding the bronchia 2, measurement information such as the two-dimensional image information regarding the branches of the bronchia 2 or the position, the bronchial diameter, the distance to the predetermined position in the bronchia 2, etc., which are corresponding to the position of the image pickup unit 16 in the bronchia 2, in the three-dimensional image data of the bronchia 2 extracted by the bronchia extracting section 23 based on the position information of the image pickup unit 16 inserted into the bronchia 2.

For example, as shown in FIG. 2B, the hollow lumen in the three-dimensional shape in the bronchia shape virtual image 2a (virtually displaying a shape of the bronchia 2 based on the CT image data) has branch portions branching into many bronchioles. In FIG. 2B, branch portions B1-B5 are shown for a case where the insertion portion 11 of the endoscope 3 is inserted from a distal end side thereof along the route set by the route setting section 30. Besides, FIG. 2B shows the branch portions B1-B5, but the embodiment is not limited to the case of the branch portions B1-B5, and is applicable to branch portions B1-Bn (n is a natural number equal to or greater than 2).

In the present embodiment, in order to smoothly perform the insertion support, the feature information acquisition section 25a acquires the two-dimensional VBS images as the two-dimensional image information from the VBS image storage section 24b (of the VBS image processing section 24), which corresponds to cases of picking up images of branch portions Bi (i=1, 2, ..., n) by the image pickup unit 16 of the endoscope 3 virtually arranged in the vicinity of the respective branch portions Bi, using the image data of three-dimensional shape of the bronchia 2.

Further, the associated image generating section 25b generates an associated image J with VBS images Ii representing images of the branch portions as the two-dimensional image information acquired by the feature information acquisition section 25a to be associated with the bronchia shape virtual image 2a as the image information of the three-dimensional shape of the bronchia 2. Then, the monitor 26 displays the associated image J as shown in FIG. 2B.

In FIG. 2B, the state where the VBS image Ii of the branch portions Bi is associated with the branch portion Bi is shown. It is noted that a central line of the lumen of the bronchia 2 (the bronchia shape virtual image 2a) is shown as indicted by the reference sign C in FIG. 2B.

Figure 3:
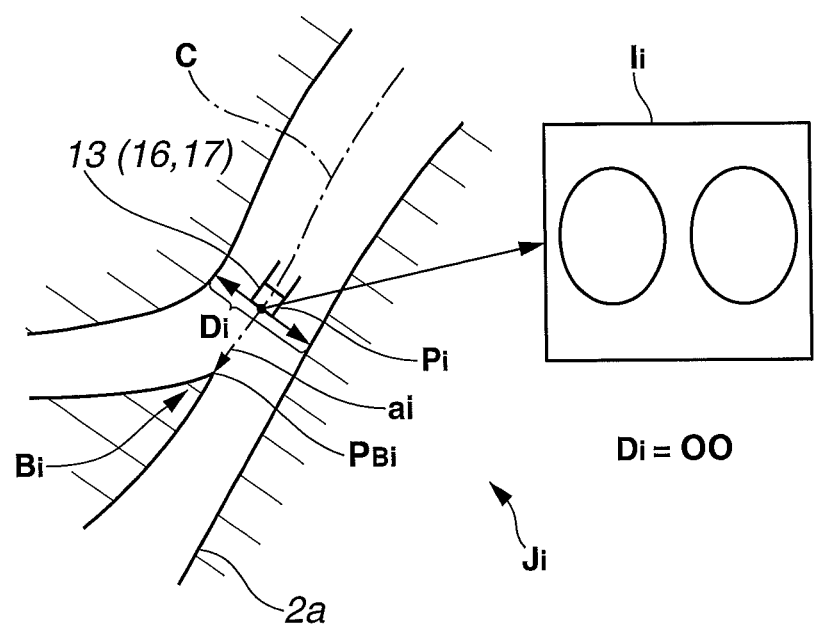
FIG. 3 is a diagram showing details of a periphery of one branch portion in FIG. 2.

FIG. 3 shows contents of association of the VBS image Ii obtained by picking up an image of one branch portion Bi in the vicinity of the branch portion Bi in more detail.

FIG. 3 shows a branch portion Bi peripheral region forming the branch portion Bi in which one luminal shape (in the bronchia 2) bifurcates into two luminal shapes at a branch boundary position PBi.

Further, FIG. 3 shows a state where the image pickup unit 16 (or the distal end portion 13 or the position sensor 17) is arranged at a position Pi on the central line C of the lumen which is away from the branch boundary position PBi by a predetermined distance ai, the branch boundary position PBi being a predetermined position in (the bronchia 2 or) the bronchia shape virtual image 2a. It is noted that specifying of the position Pi separate by the predetermined distance ai on the central line C of the luminal path will be described later in FIG. 7.

The associated image generating section 25b generates the associated image J having an associated image Ji in which the VBS image Ii corresponding to a case of picking up an image of the branch portion Bi by the image pickup unit 16 is associated with the branch portion Bi of the bronchia 2.

Further, in the present embodiment, the feature information acquisition section 25a acquires bronchial diameters Di as inner diameters of the bronchia 2 as measurement information at respective positions Pi in FIG. 3 from the image information of the three-dimensional shape of the bronchia 2. Then, the display control section 27a performs control for displaying the bronchial diameter Di on the monitor 26. Further, the storage section 28, for example, stores measurement information of the bronchial diameter Di. Besides, it is not limited to the case where the bronchial diameter Di is acquired from the image information of the three-dimensional shape of the bronchia 2, and the measurement information of the bronchial diameter Di may be acquired using a stereoscopic measurement as described later.

The determination section 27d of the control section 27 determines whether or not the position information of the image pickup unit 16, which is inserted into the bronchia 2 and the position of which is measured by the measurement processing section 18, is estimated within a predetermined condition which is allowable in the state of being actually inserted into the bronchia 2 using the position information of the three-dimensional shape of the bronchia 2 and the bronchial diameter Di stored in the storage section 28. The control section 27, if it is determined that the estimation can be performed within the predetermined condition, continues the operation of the insertion support, and if it is determined that a position displacement occurs under the predetermined condition (in other words, the position estimation results in failure), controls to calculate information of the branch portion of the bronchia 2 in the vicinity of the position of the failure.

Further, the control section 27 controls the image processing section 25 to synthesize the calculated bronchia shape virtual image 2a including the branch portions, and the VBS images for insertion support, and performs control to display a restart screen, as a display frame when restarting, on the monitor 26.

When restarting, the control section 27 displays the position of the image pickup unit 16 for restarting (i.e. the position of the image pickup unit 16 where the position estimation results in failure) on the bronchia shape virtual image 2a, and displays the VBS image in the vicinity of this position to thereby present images for facilitating correction of the position correspondence information stored in the storage section 28.

It is noted that the VBS image to be displayed is a branch portion satisfying a condition expression using at least one of the following conditions.

(I) a VBS image of a branch in which a difference between a bronchial diameter calculated from the endoscopic image and a bronchial diameter at the branch position that has calculated in advance from the CT image is not more than a threshold value.

(II) a VBS image for a branch portion located within a certain range from the position where the position estimation lastly results in success, (III) a VBS image for a branch portion located within a certain range from the position where the position estimation results in failure, (IV) a VBS image for a branch portion in the vicinity of the position which is stored in the storage section 28 within a certain period from the time when the position estimation results in failure, and (V) a branch portion on the route.

Further, a distance from a distal end of the endoscope to a branch is calculated from the endoscopic image and a VBS image at a position away from the branch portion satisfying the above condition by the same distance may be generated.

The distance in these conditions may be a distance between two points in a straight line or a way on the central line of the lumen.

The medical apparatus 1 having the above configuration includes: the CT image data storage section 22 that constitutes storage means for storing three-dimensional image information in a subject, the three-dimensional image information being acquired in advance; the image pickup unit 16 that constitutes image pickup means for picking up an image in the subject; the bronchia extracting section 23 that constitutes luminal organ extracting means for extracting image information of a three-dimensional shape of the bronchia 2 as a specific luminal organ in the subject from the three-dimensional image information; the feature information acquisition section 25a that constitutes feature information acquisition means for acquiring feature information in the image information of the three-dimensional shape of the specific luminal organ extracted by the luminal organ extracting means based on the position information of the image pickup means inserted into the specific luminal organ; the associated image generating section 25b that constitutes associated image generating means for generating an image in which the feature information is associated with the image information of the three-dimensional shape of the specific luminal organ; the monitor 26 that constitutes display means for displaying the feature information in the vicinity of the position information of the image pickup means in the specific luminal organ.

Figure 4:
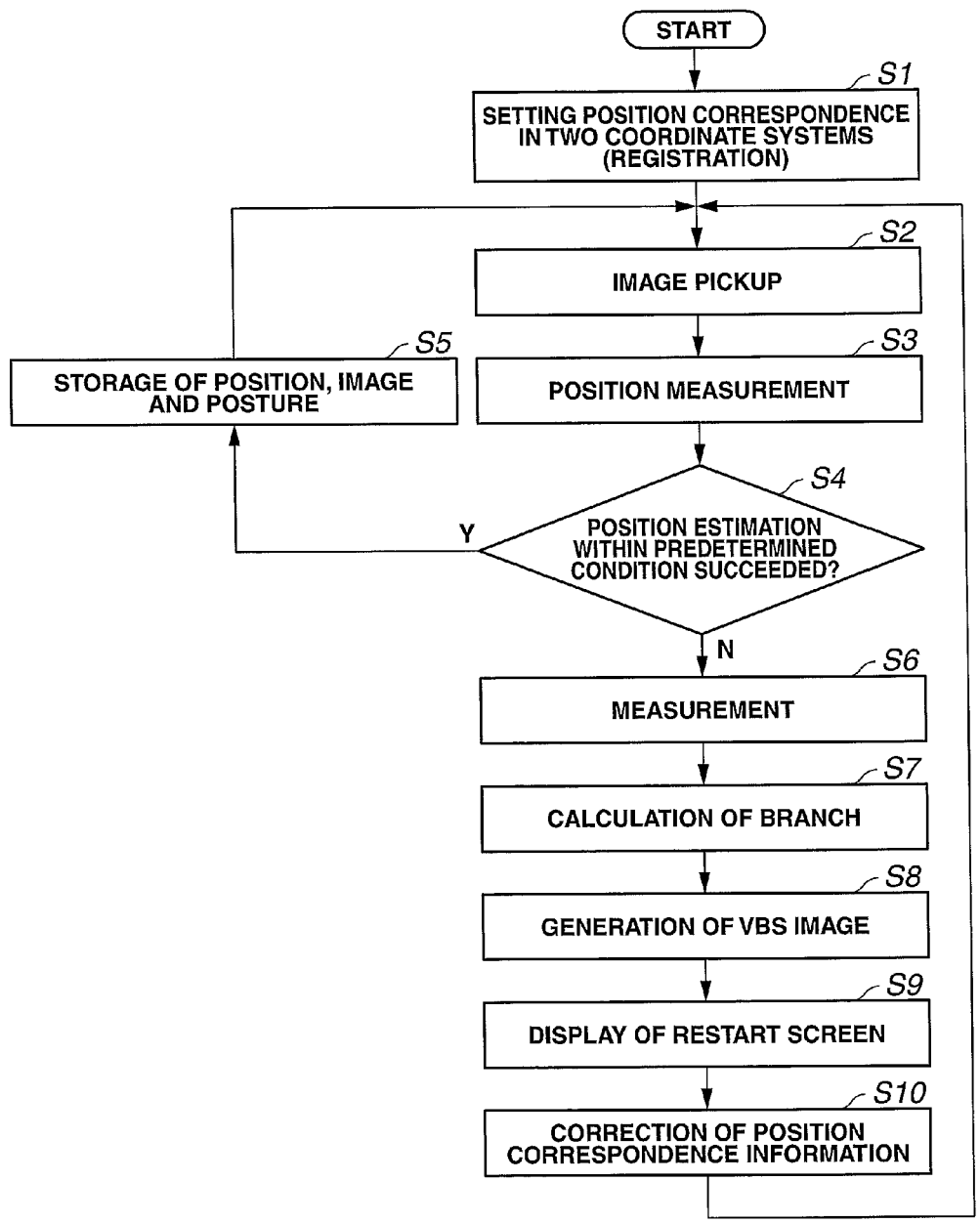
FIG. 4 is a flowchart showing processing contents of an insertion support by the medical apparatus when an insertion portion of the endoscope is inserted into the bronchia.

Next, operations in the present embodiment will be described referring to FIG. 4. FIG. 4 shows primary processing of respective sections of the medical apparatus 1 when the insertion portion 11 of the endoscope 3 into the bronchia 2.

When inserting the insertion portion 11 of the endoscope 3 into the bronchia 2, the control section 27 of the medical apparatus 1 performs processing for setting position correspondence (registration) in the coordinate systems, as shown in step S1.

The control section 27 (the position correspondence control section 27d thereof) performs processing of setting position correspondence (registration) for setting correspondence at a plurality of positions, that are three or more positions, between the first coordinate system used for the CT image data and in extracting the image data of the three-dimensional shape of the bronchia 2 from the CT data, and the second coordinate system for use in measurement of the position sensor 17 in the distal end portion 13 by the measurement processing section 18.

Figure 5:
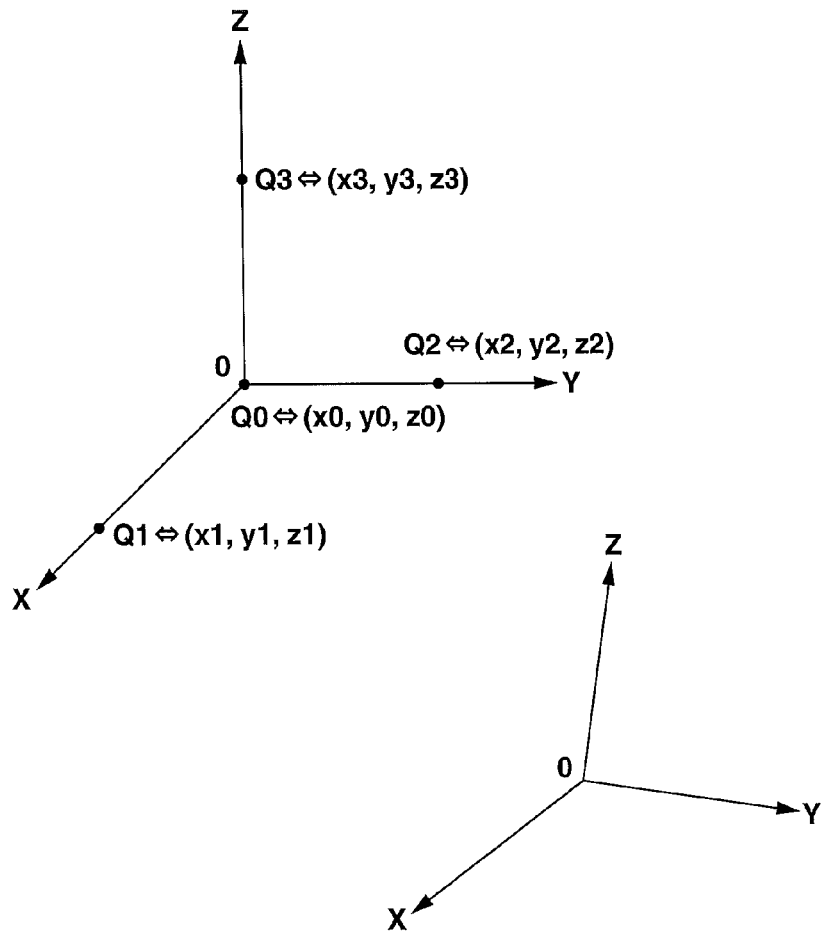
FIG. 5 is an explanatory diagram when setting correspondence of the same position in two coordinate systems.

FIG. 5 shows an explanatory diagram of operations for setting the position correspondence. For example, the surgeon sequentially sets the distal end portion 13 (or the position sensor 17) of the endoscope 3 at four points Q0-Q3, for example, in the vicinity of an entrance of the bronchia 2, and performs instructions or instruction inputs for setting position correspondence in a first coordinate system O-XYZ and in a second coordinate system o-xyz through the input unit 31. Therefore, the input unit 31 forms an instruction input section or input instruction means for performing an instruction for setting the position correspondence.

For example, the distal end portion 13 (or the position sensor 17) is sequentially set to the position Q0 (0, 0, 0) of an origin O, the position Q1 (1, 0, 0) on an X coordinate axis, the position Q2 (0, 1, 0) on a Y coordinate axis and the position Q3 (0, 0, 1) on a Z coordinate axis in the first coordinate system O-XYZ, and the surgeon performs instructions for setting the position correspondence. Assuming, in these instructions, that coordinate positions respectively measured by the measurement processing section 18 at the respective positions are (x0, y0, z0), (x1, y1, z1), (x2, y2, z2) and (x3, y3, z3), respectively, the control section 27 performs setting of the position correspondence and performs control to store position correspondence information in the storage section 28.

The storage section 28 stores the position correspondence information on this occasion (specifically, Q0 (0, 0, 0), Q1 (1, 0, 0), Q2 (0, 1, 0) and Q3 (0, 0, 1) in the first coordinate system O-XYZ, and (x0, y0, z0), (x1, y1, z1), (x2, y2, z2) and (x3, y3, z3) in the second coordinate system o-xyz, respectively, being corresponding information).

Further, the control section 27 determines conversion information for setting correspondence of an arbitrary position between the two coordinate systems using the position correspondence information stored in the storage section 28. The control section 27 makes the conversion information be stored in the storage section 28.

In FIG. 5, the coordinate positions Q0 (0, 0, 0), Q1 (1, 0, 0), Q2 (0, 1, 0), Q3 (0, 0, 1) and the respectively corresponding coordinate positions (x0, y0, z0), (x1, y1, z1), (x2, y2, z2), (x3, y3, z3) are shown as Q0 ⇔ (x0, y0, z0), Q1⇔ (x1, y1, z1), Q2⇔ (x2, y2, z2) and Q3⇔ (x3, y3, z3) for simplification. It is noted that the position correspondence may be performed (determined) using three points with one point omitted, instead of the four points as shown in FIG. 5.

After completing the processing of setting position correspondence as described, the surgeon starts performing an endoscopic examination by inserting the insertion portion 11 of the endoscope 2 into the bronchia 2.

The surgeon makes an input for an instruction to display the bronchia shape virtual image 2a of the three-dimensional shape of the bronchia 2 on the monitor 26, so that the bronchia shape virtual image of the three-dimensional shape of the bronchia 2 on the monitor 26 and further makes setting of a route (path) of inserting the insertion portion 11 of the endoscope 3 into the bronchia 2, etc.

When the surgeon inserts the insertion portion 11 of the endoscope 3 from a side of the distal end portion 13 into the bronchia 2, the image pickup unit 16 in the distal end portion 13 picks up an image inside the bronchia 2 as shown in step S2 of FIG. 4, so that a picked-up image is displayed on the monitor 9 and also displayed on the monitor 26.

Further, as shown in step S3, the measurement processing section 18 performs measurement of the position of the position sensor 17 or the distal end portion 13 (or the image pickup unit 16), and outputs position data obtained by the position measurement to the control section 27.

As shown in step S4, the control section 27 determinates whether or not the position data in the second coordinate system inputted from the measurement processing section 18 is successful in position estimation within a predetermined condition, with respect to the position data in the first coordinate system which represents the three-dimensional shape of the bronchia 2.

Figure 6:
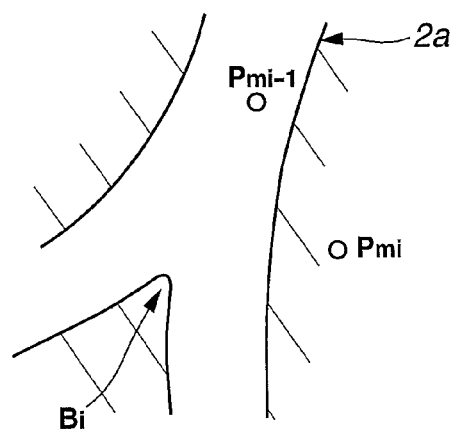
FIG. 6 is an explanatory diagram for explaining determination on whether or not a measured position of an image pickup unit is located within a lumen under a predetermined condition when the insertion portion of the endoscope is inserted into bronchia.

As one method for determination of the position estimation within the predetermined condition, for example, as shown in FIG. 6, a method in which a measured position Pmi in the second coordinate system obtained at i-th measurement, for example, by the measurement processing section 18 exists inside of the luminal shape of the bronchia 2 in the first coordinate system is adopted.

As shown in in FIG. 6, with respect to a measured position Pm(i−1) obtained at (i−1)th measurement, if the position is calculated to exist in a region inside the lumen in the bronchia shape virtual image 2a in the first coordinate system, the determination section 27d determines that the position estimation within the predetermined condition is successful. It is noted that the outside of the luminal shape is shown by hatching in FIG. 6.

In this manner, if the determination section 27d determines that the position estimation within the predetermined condition is successful, the control section 27 controls, in next step S5, to store the measured position Pm(i−1) which is determined to be successful in position estimation within the predetermined condition, the picked-up image by the image pickup unit 16, information of a posture of the distal end portion 13 and information of time at which the measurement is performed in the storage section 28.

Thus, the storage section 28 includes a position/image storage section 28b that stores the position information of the image pickup unit 16 which is inserted into the bronchia 2, the picked-up image obtained by image pickup unit 16 and the information of the posture of the distal end portion 13 in time series. Besides, it is not limited to a case where the position estimation is successful, it may be configured that, when the position estimation results in failure not in success, the storage section 28 stores the above information in time series.

After the processing of step S5, the procedure returns to the processing of step S2 and repeats the processing of steps S2-S5.

By contrast, as shown in FIG. 6, the measured position Pmi obtained at i-th measurement is calculated as being located in a region as shown by the hatching which is outside of the lumen in the first coordinate system, the determination section 27d determines that the position estimation within the predetermined condition has failed.

In this case, the procedure proceeds to processing of step S6 in which the control section 27 controls the measurement processing section 18 to perform the measurement. Then, in step S7, the measurement processing section 18 acquires branch portions in the vicinity of the measured position Pmi from the image data of the three-dimensional shape of the bronchia extracting section 23, and obtains the bronchial diameters from the feature information acquisition section 25a. Further, a bronchial diameter Ri at the branch portion is acquired by the stereoscopic measurement using the endoscopic images at the measured positions Pmi and Pm−1, and calculates a branch with a bronchial diameter which has a difference from the bronchial diameters obtained from the feature information acquisition section 25a being equal to or less than a threshold.

Besides, it is not limited to the case of one branch portion Bi as described above, but it may be configured that the control section 27 calculates a plurality of branch portions in order to increase options for the surgeon.

Further, in step S8, the control section 27 generates a virtual endoscopic image, i.e. a VBS image in the vicinity of the branch portion Bi. Then, in the next step S9, the control section 27 controls the associated image generating section 25b of the image processing section 25 to generate an associated image and display the image on the monitor 26 as a restart screen. As the image in the restart screen, an associated image Ji as shown in FIG. 3 is displayed.

Since the associated image Ji is presented by the display on the monitor, the surgeon performs a countermeasure when the position estimation has failed, e.g. processing of correcting the setting of the position correspondence, as shown in step S10. The procedure returns to the processing of step S2 after the processing of step S10. Besides, it may be configured that the plurality of branch portions and the plurality of VBS images are displayed. Further, it may be configured that the number of branch portions and the number of VBS images to be displayed can be selectively set by the surgeon.

Next, processing operations for correcting the position correspondence information in the associated image Ji or the restart screen will be described.

In FIG. 6, if the measured position Pmi is outside of the lumen, the control section 27 performs control for calculating the branch portion Bi in the vicinity of the measured position Pmi and performs control for displaying the associated image Ji on the monitor, as shown in FIG. 3.

The surgeon corrects the position correspondence information set in the initialization through the display of the associated image Ji in the following manner to thereby make it possible to smoothly continue the insertion operation of the endoscope 3.

The operations for correcting the position correspondence information which has a large error in the position correspondence using the image of FIG. 3 will be described.

Figure 7:
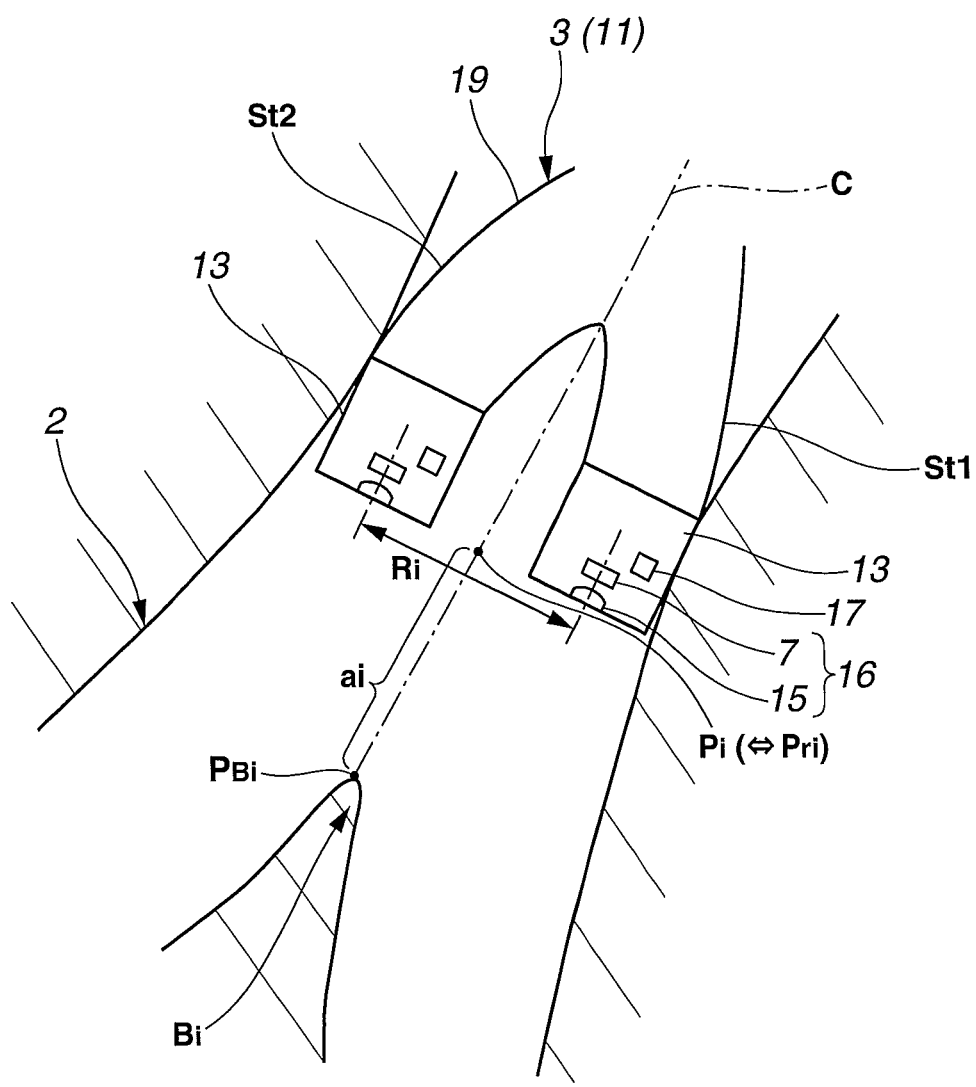
FIG. 7 is an explanatory diagram for explaining correction of position correspondence information by newly setting a reference position in a restart screen.

FIG. 7 shows an explanatory diagram for correction of the position correspondence information by specifying a position Pi as a reference position in a state of the bronchia 2 and the distal end side of the endoscope 3 inserted into the bronchia 2, which corresponds to the state of FIG. 3. Further, FIG. 8 shows operations and processing for correcting the position corresponding information.

Figure 8:
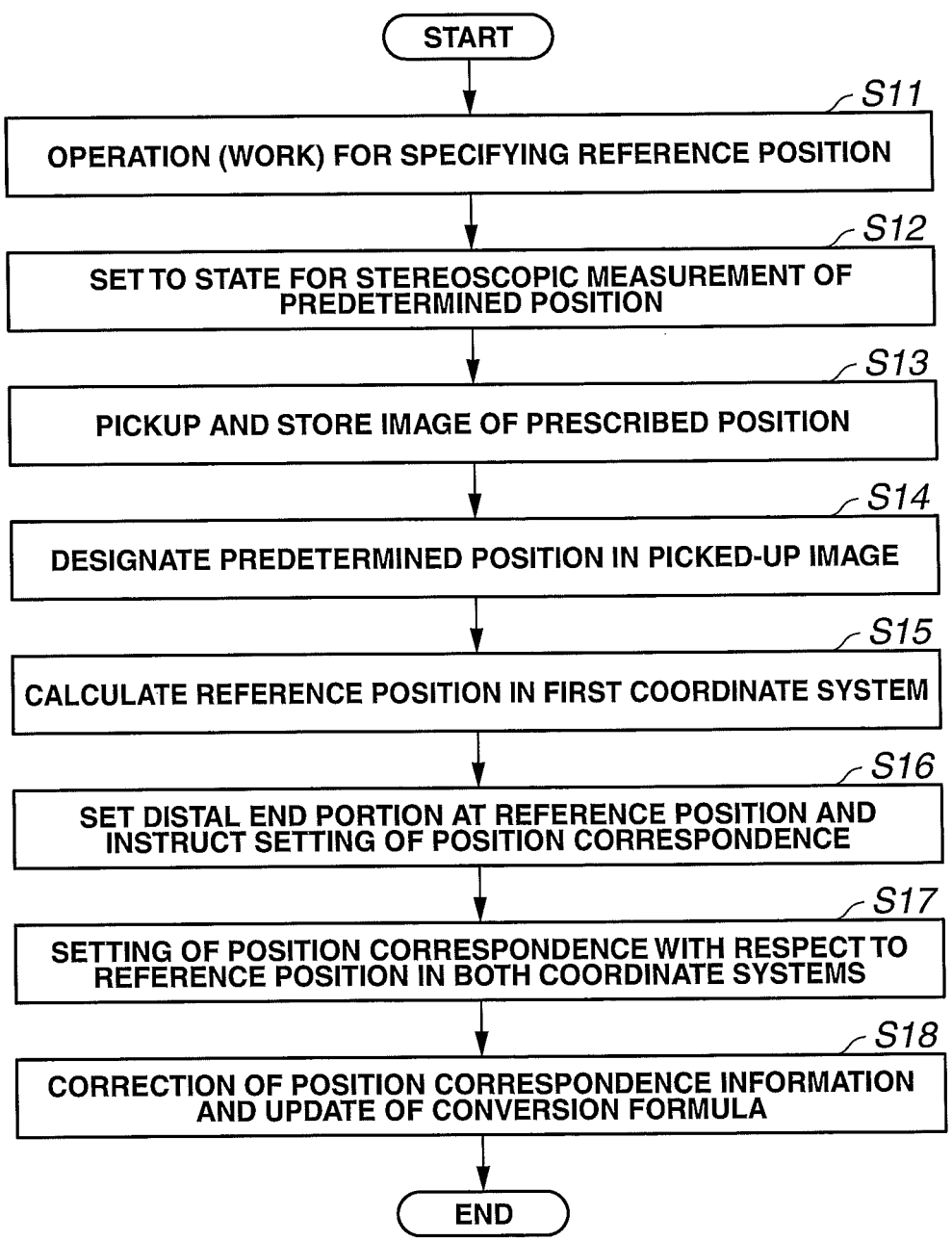
FIG. 8 is a flowchart showing processing of correcting the position correspondence information by specifying the reference position.

The surgeon performs an operation (work) for specifying the reference position as shown in step S11 of FIG. 8. In order to correct the position correspondence information set in the initialization, an operation of newly setting the reference position is performed. Since a three-dimensional position of a branch boundary position PBi in the first coordinate system is located at an apex which projects inside the lumen in the image data of the three-dimensional shape of the bronchia 2, this position is a specific position which is easy to be specified.

Further, in order to specify a position Pi which is away from the branch boundary position PBi by the predetermined distance ai on the central line C of the lumen of the bronchia 2 as the reference position, the surgeon sets the image pickup unit 16 of the endoscope 3 to be in a state for performing a stereoscopic measurement of the branch boundary position PBi as the predetermined position, as shown in step S12.

In a case of the endoscope 3 having only one image pickup unit 16, the surgeon bends the bending portion 19 of the endoscope 3 to sequentially set two states St1 and St2 in contact with an inner wall of the lumen.

Then, as shown in step S13, images of the branch boundary position PBi in the respective states St1 and St2 are picked up by the image pickup device 16, and the picked-up images are stored, for example, in the storage section 28.

As shown in step S14, the surgeon designates the branch boundary position PBi as the same predetermined position in the two picked-up images through the input unit 31.

As shown in step S15, based on the designation, the control section 27 calculates the distance ai using information of a focal length of the objective lens 15 of the endoscope 3, a size and the number of pixels of an image pickup surface of the image pickup device 7, etc. and calculates a three-dimensional position of the position Pi as the reference position in the first coordinate system.

In the next step S16, the surgeon sets the distal end portion 13 at the position Pi, and performs an instruction for setting the position correspondence through the input unit 31.

Upon receiving the instruction, in step S17, the control section 27 performs processing of newly setting the position correspondence at the position Pi as the reference position in the first coordinate system and in the second coordinate system.

That is, the control section 27 performs processing of setting correspondence of a position Pri in the first coordinate system at which the position measurement of the position Pi is performed in the second coordinate system.

Further, in step S18, by the information of the position correspondence, the control section 27 corrects the position correspondence information in the initialization.

For example, the control section 27 generates corrected position correspondence information from the information of the position correspondence of FIG. 7 and the three pieces of position correspondence information in the position correspondence information set in the initialization. Further, the conversion formula for conversion or setting correspondence between a position in the first coordinate system and a position in the second coordinate system is corrected (updated).

The position correspondence information acquired at the position Pi as shown in FIG. 7 is considered to be position information having higher reliability when the insertion portion 11 of the endoscope is actually inserted, since this position correspondence information is position correspondence information acquired at a deeper side along the luminal path of the bronchia 2 in comparison with the position correspondence information in the initialization which has been set in the vicinity of the entrance of the bronchia 2. Thus, by correcting the position correspondence information in the initialization by the acquired position correspondence information, a correction error can be corrected by the position correspondence information at the deeper side along the luminal path of the bronchia 2.

Then, in this manner, the surgeon continues the insertion operation using the corrected position correspondence information. For example, the surgeon performs an instruction to restart the position measurement in the restart screen through the input unit 31 and thereby the processing subsequent to step S2 in FIG. 4 is restarted using the corrected position correspondence information.

Thus, it is possible to support the surgeon in performing the operation of smoothly inserting the endoscope 3 into a deeper side of the bronchia 2 by using the information of insertion support in the medical apparatus 1.

Figure 9:
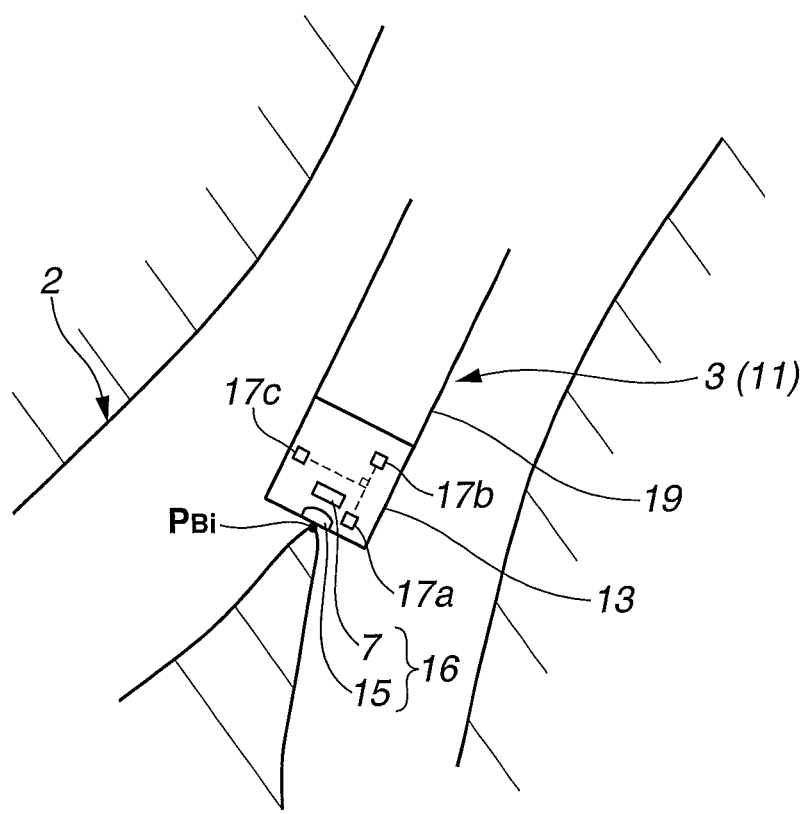
FIG. 9 is an explanatory diagram showing a manner of performing position correspondence by setting a distal end portion of the endoscope at a predetermined position in the bronchia.

Besides, an example of setting the position correspondence between the two coordinate systems at the reference position using the stereoscopic measurement is explained in the above description, but it may be configured that the position correspondence between the two coordinate systems is performed at the branch boundary position Pbi in a state where a distal end face of the distal end portion 13 is brought into contact with the branch boundary position Pbi, as shown in FIG. 9.

In this case, it can be configured that the insertion support apparatus 5 performs the processing of position correspondence of FIG. 8 only by setting of the distal end face of the distal end portion 13 to be in a state of being in contact with the branch boundary position Pbi as the predetermined position and inputting of the instruction for setting the position correspondence to the control section 27 through the input unit 31, by the surgeon. Further, the position correspondence information may be corrected by using the method described in Japanese Patent Laid-Open Publication 2009-279251, that is, the method of obtaining a position and a posture of an endoscope distal end by searching a VBS image similar to an endoscopic image. Alternatively, the position correspondence information may be corrected, using the position of the endoscope distal end calculated by this method and three points selected from among the four points used in calculating the initial position correspondence information, according to the foregoing method.

Further, a plurality of position sensors may be arranged as shown in FIG. 9 to be substituted for the position sensor 17 provided at the distal end portion 13. In the case where the plurality of position sensors 17 are arranged, a direction (orientation) of picking up an image by the image pickup unit 16 at the distal end portion 13 can be detected by providing, in addition to the position sensors (17a, 17b) arranged along an axial direction (longitudinal direction) of the insertion portion 11, a position sensor (17c) which is disposed in a direction orthogonal to the axial direction, for example. The direction (orientation) of picking up an image by the image pickup unit 16 is referred as a direction of line of sight. When storing the position of the image pickup unit 16 in the storage section 28, the information of the direction of line of sight may be also stored.

Besides, the position estimation within the predetermined condition is determined in step S4 of FIG. 4 on the determination condition of whether or not the position obtained by position measurement in the second coordinate system is inside of the bronchial diameter in the first coordinate system, but it may be combined with a determination condition that the measured position is within a preset distance from the position where the position correspondence has been performed.

In this case, in step S4 of FIG. 4, it may be configured that it is determined that the determination condition of the position estimation within the predetermined condition is not fulfilled if a certain distance R from the position where the position correspondence was performed in the past is exceeded, and the procedure proceeds to the processing of step S6.

Further, a still another determination condition may be adopted as the determination condition in step S4.

Other than the position sensor 17 for performing the position measurement of the distal end portion 13 of the endoscope 3, it may be configured that, when a position sensor (an extracorporeal marker) for correcting organs' movements caused by patient's breathing is moved in an unexpected direction or the extracorporeal marker detects a motion amount not less than a certain amount, the determining section 27d of the control section 27 determines that the determining condition of the position estimation within the predetermined condition is not fulfilled in step S4 and the procedure proceeds to the processing of step S6.

Moreover, it may be configured such that two or more of the above described methods, i.e. the bronchial diameter, the distance and the motion amount not less than the certain amount are combined.

According to the above-described first embodiment, when the insertion portion 11 of the endoscope is inserted into the bronchia 2 as the specific luminal organ, the medical apparatus 1 measures the position of the image pickup unit 16 provided at the distal end portion 13 of the insertion portion 11, and displays the virtual endoscopic image inside the bronchia 2 in the vicinity of the measured position, the bronchial diameter, the distance to the predetermined position, etc. on the monitor 26, and therefore, in the case of failing in the position estimation of the image pickup unit 16, it is possible to present the surgeon with the information which facilitates to deal with the failure in the position estimation.

For example, in the restart screen displayed on the monitor 26 when the position estimation has failed, by correcting the position correspondence information in the two coordinate systems using the stereoscopic measurement as described in FIG. 8, it is possible to perform the support such that the operation of inserting the insertion portion 11 of the endoscope 3 into the deeper side of the bronchia 2 can be continued again from the restart screen. As a simpler method, the position correspondence information may be corrected by bringing the distal end face of the distal end portion 13 of the endoscope 3 into contact with the branch boundary position as the predetermined position of the bronchia 2.

By combining the plurality of conditions in the above-described step S4, the following effects are obtained. Specifically, when two or more conditions from among the conditions that "located out of the bronchia", "within the certain distance from the position where the setting of the position correspondence was performed in the past" and "the motion amount not less than the certain amount" are combined by using "or" to define a determination formula, it is made possible to perform the detection even when an error in the correction of the position correspondence information is small, and to perform the position display of the distal end of the endoscope with high precision. Further, when the two or more conditions are combined by using "and", robustness of the determination is improved and therefore it is possible to prevent an increase of the number of restarts even if precision of the position sensor is lowered by noise or the like.

Further, in step S9, by specifying and narrowing the VBS image to be displayed on the restart screen using the measurement information of "the bronchial diameter" and "the distance to the branch portion", the selection of the VBS image by the surgeon is made easy.

Besides, in the foregoing embodiments, in the case where the position estimation does not result in failure as well, the image processing section 25 may generates an image in which the feature information is associated with the image information of the three-dimensional shape of the bronchia 2 as the specific luminal organ and the control section 27 may control to display the feature information of the bronchia 2 (which is acquired by the feature information acquisition section 25a) in the vicinity of the position information of the image pickup unit 16 on the monitor 26. In this case, by displaying the VBS image of the branch portion, for example, in the vicinity of the image pickup unit 16 as the feature information, the operation of insertion is made easy since the surgeon can perform the operation at the branch portion while confirming which side of the luminal paths the distal end portion 13 should be inserted into.

Further, as the measurement information of measuring the distance to the predetermined position as the measurement information in the above-described cases, an example of the distance from the position of the image pickup unit 16 to the predetermined position in the branch portion Bi is described, but the distance from the position of image pickup unit 16 to a branch point at which the central line C of the luminal path of the bronchia 2 branches in a branch portion Bi may be set as the measurement information, as described in the following embodiment.

(Second Embodiment)

Figure 10:
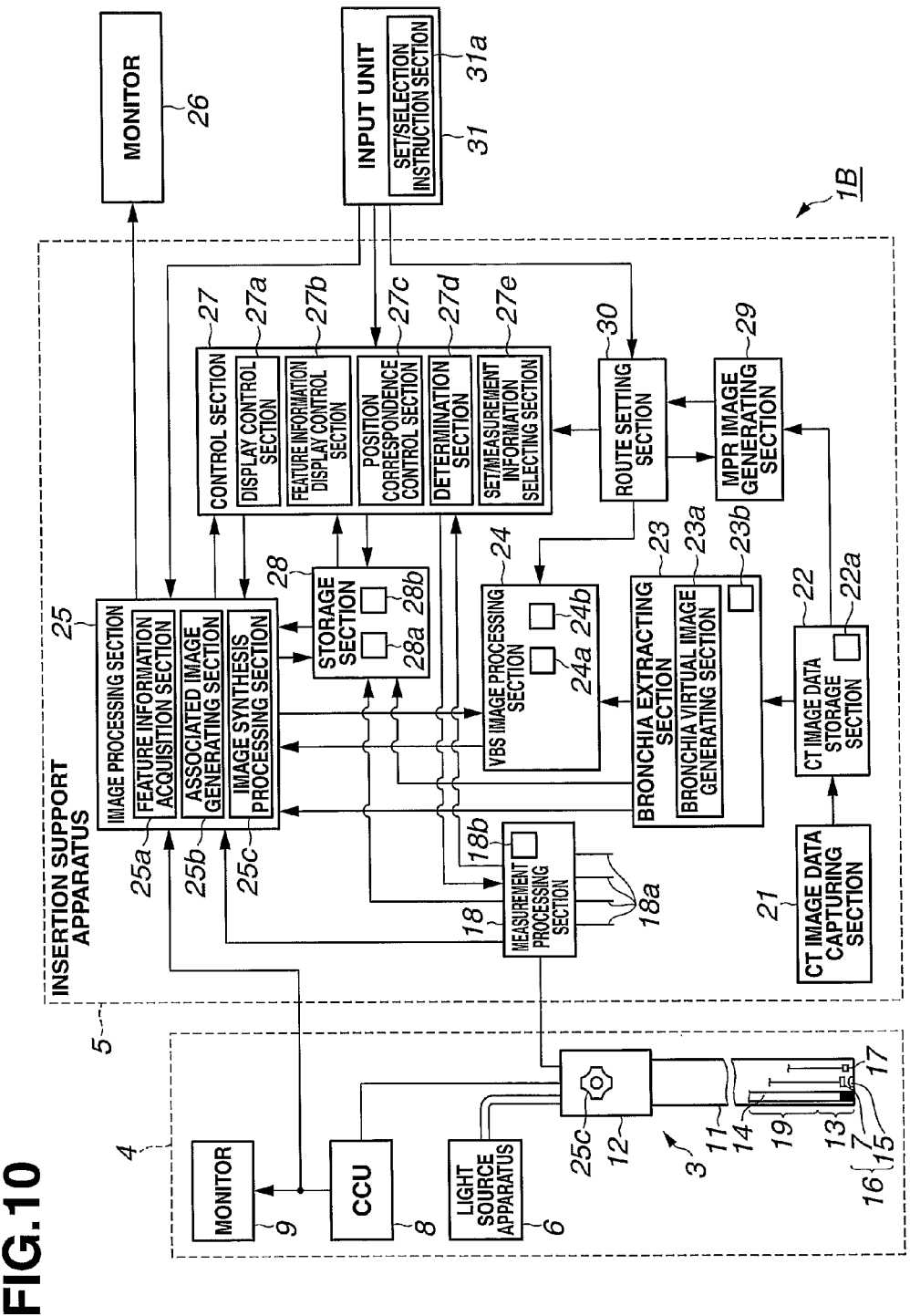
FIG. 10 is diagram showing an entire configuration of a medical apparatus according to a second embodiment of the present invention.

Next, the second embodiment of the present invention will be described. A medical apparatus 1B in the present embodiment as shown in FIG. 10 has a configuration in which selection means for setting regions in the bronchia 2 and performing selection to switch measurement information for each region is provided in the configuration of the medical apparatus 1 as shown in FIG. 1. If the selection means is not used, this embodiment has the same configuration and the same functions as the first embodiment.

As the above selection means, for example, the input unit 31 includes a set/selection instruction section 31a for performing set/selection instructions for setting the regions and selecting measurement information for each region, and the control section 27 includes a setting/measurement information selection section 27e that performs setting of the regions and control of selection of the measurement information for each region in response to the set/selection instructions. The other configurations are the same as the first embodiment.

Figure 11:
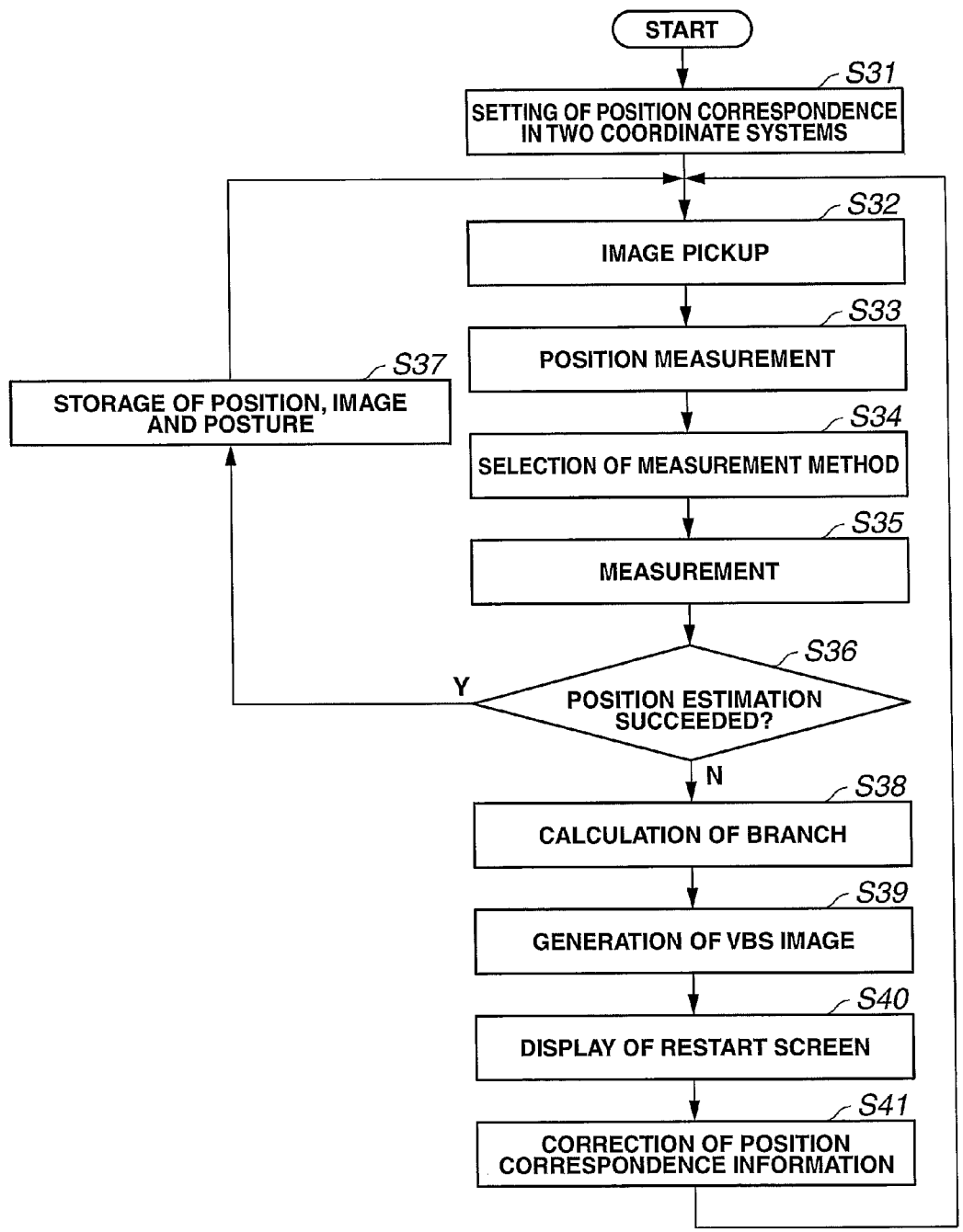
FIG. 11 is a flowchart showing processing contents of an insertion support by a medical apparatus when inserting the insertion portion of the endoscope into the bronchia in the second embodiment of the present invention.

FIG. 11 shows processing contents in the present embodiment. It is noted that steps S31-S33 and S35-S37 are substantially the same processing as those in the first embodiment.

As shown in FIG. 11, in the first step S31, the control section 27 performs control of setting the position correspondence in the two coordinate systems in the same manner as step S1 of FIG. 4.

In the next Step 32, the image pickup unit 16 performs an image pickup and further in step S33, the measurement processing section 18 performs position measurement of the distal end portion 13 (or the image pickup unit 16).

In the next step S34, the setting/measurement information selection section 27e of the control section 27 selects a measurement method for a region in which the distal end portion 13 (or the image pickup unit 16) is detected to be located by the position measurement.

Figure 12:
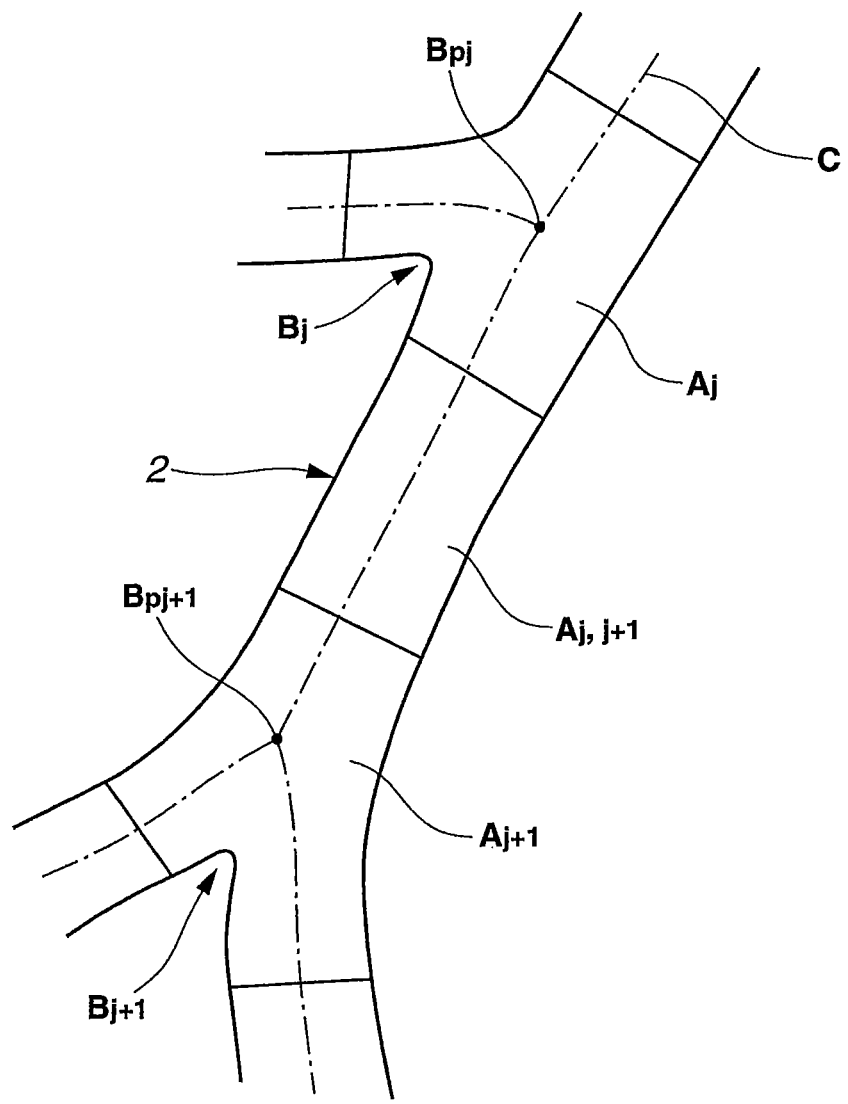
FIG. 12 is an explanatory diagram for explaining a manner of selectively setting measurement information for each region set in the bronchia.

FIG. 12 shows a setting example in the case where it is set such that the measurement method is selected for the region in which the distal end portion 13 (or the image pickup unit 16) is located.

As shown in FIG. 12, regions Aj, Aj+1 within certain distances from branch points Bpj, Bpj+1 in branch portions Bj, Bj+1, and regions Aj, j+1, . . . in between are set along the central line C of the lumen of the bronchia 2. It is noted that the branch points Bpj, Bpj+1 are defined as points at which one central line C branches into a plurality of lines, e.g. two lines in the vicinity of the branch portions Bj, Bj+1.

Then, when the distal end portion 13 (or the image pickup unit 16) is located in the region Aj, for example, in the lumen of the bronchia 2, the measurement information is set to the position, when the distal end portion 13 (or the image pickup unit 16) is located in the region Aj, J+1, the measurement information is set to the distance, and when the distal end portion 13 (or the image pickup unit 16) is located in the region Aj+1, the measurement information is set to the bronchial diameter. It is noted that in the case where the measurement information is the position or the distance, the information is acquired by position measurement by the measurement processing section 18.

On the other hand, in the case where the measurement information is the bronchial diameter, the bronchial diameter is measured by the stereoscopic measurement as described in FIG. 7.

Further, the illustrated example of FIG. 12 shows one setting example and the surgeon is allowed to perform setting different from the illustrated example of FIG. 12 through the set/selection instruction section 31a of the input unit 31. That is, it is possible to acquire and display the measurement information by the measurement method which the surgeon desires.

Besides, FIG. 12 shows one setting example of regions for switching the measurement information, and the regions may be set as follows including the setting example of FIG. 12.
(A) Regions each within the certain distance from the branch point on the central line, and the other regions (the illustrated example of FIG. 12),
(B) Regions each included in a sphere having a certain radius and the branch point as a center, and the other regions,
(C) Distances from a specific position (e.g. a carina indicated by K in FIG. 2B),
(D) Degrees of the bronchia or the number of branches sequentially counted from an entering side of the bronchia,
(E) Bronchial diameters calculated from the CT tomographic images,
(F) Distances from a position of the previous restart (or start).

Here, the distance mentioned in A, C, and F may be a distance between two points in a straight line or a way on the central line of the lumen.

Further, two or more of these conditions may be combined.

In step S35 subsequent to step S34, the measurement processing section 18 and so forth perform measurement in accordance with the region in which the distal end portion 13 (or image pickup unit 16) is located.

In the next step S36, the determination section 27d of the control section 27 determines whether or not the position estimation by the measurement performed in S35 has succeeded.

As described in the first embodiment, one of the conditions that the position measured in the second coordinate system is present: (a) within the bronchial diameter, (b) within the certain distance from the position at which the setting of the position correspondence was performed in the past, and (c) within a certain motion amount in the patient on the basis of the sensor and the like other than the position sensor 17, is used.

In step S36, when the position estimation has succeeded within the condition (a), (b), (c), the procedure proceeds to the processing of step S37. On the other hand, when the position estimation has not succeeded, the procedure returns to the processing of step S32 after performing the processing of step S38-S41.

When the position estimation has not succeeded, the processing of calculation of the branch in step S38, the processing of calculation of the VBS image in step S39, the processing of display of the restart screen in step S40 and the processing of correction of the position correspondence information in step S41 are performed and then the procedure returns to the processing of step S32. It is noted that the processing of steps S38-S41 is the same as that in steps S7-S10 of FIG. 4.

On the other hand, in step S36, when the position estimation has succeeded within the condition (a), (b), (c), the procedure returns to the processing of step S37.

In the step S37, the control section 27 performs control to store the position of the distal end portion 13 (or the image pickup unit 16) measured in the second coordinate system, the picked-up image picked up by the image pickup unit 16, the information of the posture of the distal end portion 13 (the axial direction of the distal end portion 13 or the image pickup direction), with information of time in the storage section 28, and then the procedure returns to the processing of step S32. Besides, it may be configured that the storage section 38 stores the acquired measurement information.

According to the present embodiment in which the above operations are performed, the same effects as the first embodiment are obtained and an effect that the measurement can be performed by selecting the measurement method is obtained. Hereinafter, modified examples of the second embodiment will be successively described.

First Modified Example

With regard to the processing of displaying the restart screen at the step S40 in the second embodiment, the following processing is performed in the present modified example.

The bronchial diameter is calculated form the endoscopic image.

The calculated bronchial diameter is compared with the bronchial diameters which have been calculated from the CT images in advance and a restart screen is generated by a VBS image of a branch having a diameter (approximately) equal to the calculated diameter.

Further, instead of comparison of the diameters for all the branches, the diameters may be compared for the following branches;

(d) Branches in the vicinity of the position at which the position estimation has failed,
(e) Branches in the vicinity of the position at which the position estimation has succeeded last
(f) Branches on the route, and
(g) Combination of two or more of the above conditions.

Second Modified Example

In the present modified example, the distance to the branch is calculated from the endoscopic image and the VBS images at positions away by the same distance are generated for all of the branches, to thereby generate the restart image.

Further, instead of all of the branches, the branches may be as follows;

(d) Branches in the vicinity of the position at which the position estimation has failed,
(e) Branches in the vicinity of the position at which the position estimation has succeeded last,
(f) Branches on the route, and
(g) Combination of two or more of the above conditions.

Third Modified Example

In the present modified example, the condition of the branches to be compared in the first modified example is set for each of the regions in the same manner as the second embodiment.

Fourth Modified Example

In the present modified example, the condition of the branches to be generated in the second modified example is set for each of the regions in the same manner as the second embodiment.

Further, in the foregoing first and second modified examples of the second embodiment, all of the branches that fulfill the condition are displayed, but the position information to be displayed may be limited under conditions, as shown in the following fifth to eighth modified example.

Fifth Modified Example

In the first to fourth modified examples of the second embodiment, only the positions in the past within a certain time period from the moment when the position estimation failed are displayed.

Sixth Modified Example

In the first to fourth modified examples of the second embodiment, only the positions in the past within a certain range from the position where the position estimation failed are displayed.

Seventh Modified Example

In the first to fourth modified examples of the second embodiment, only the positions at which the measurement information has changed by a value not less than a reference value are displayed.

In this case, the reference value is a value of the measurement information at the position closest to the present position in the measurement information at the position which is determined to be displayed.

Figure 13:
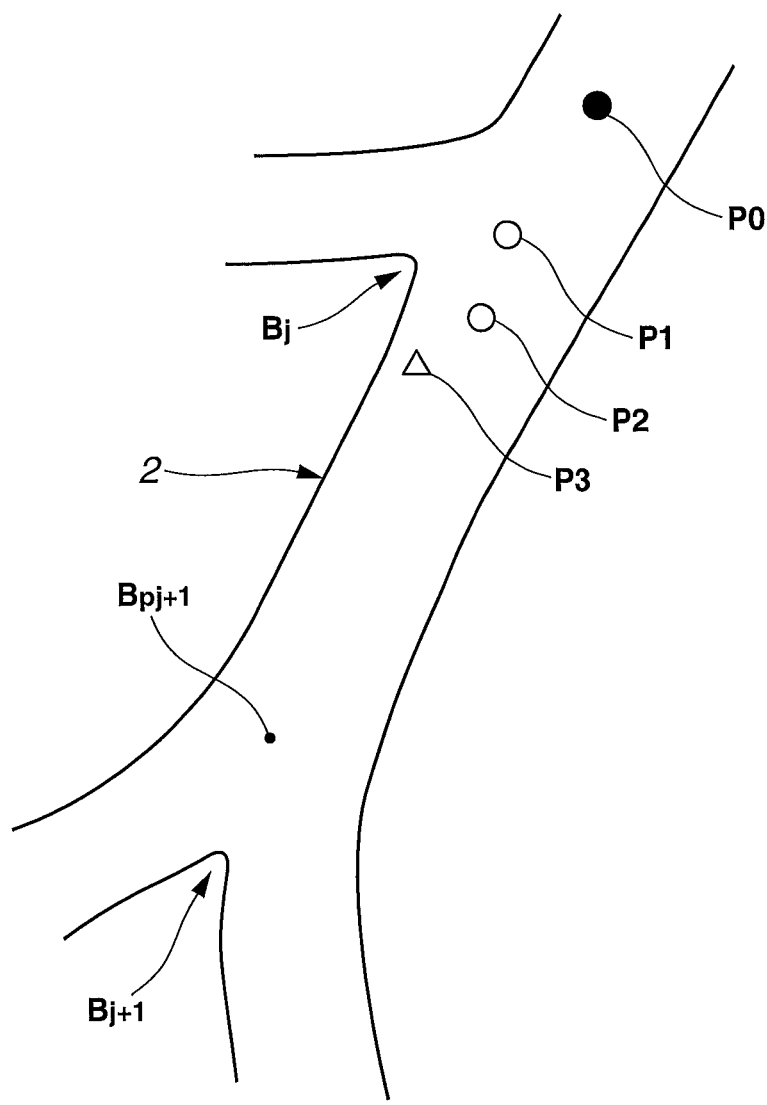
FIG. 13 is an explanatory diagram showing a present position of the image pickup unit and so forth in a seventh modified example of the second embodiment.

For example, the case in which the measurement information is set to the distance to the branch point will be described. In FIG. 13, the positions P0, P1 and P2 in the vicinity of the branch point Bj are positions at which the position estimation succeeded in the past. Further, the position P0 indicated by the black circle shows a position where the measurement information has changed by a value not less than a threshold value, and the positions P1 and P2 indicated by the white circles show positions where the measurement information is within the threshold value. Then, it is configured such that the position P0 indicated by the black circle is displayed in the restart screen.

Further, the present position is denoted by P3 in FIG. 13 and the measurement information at the present position P3 is the distance P3Bpj+1 from the present position P3 to the branch point Bpj+1 which is located at a peripheral side. Since the reference measurement information is the measurement information at the position P1 which is closest to the present position P3, the measurement information is the distance P1Bpj+1.

Figure 14:
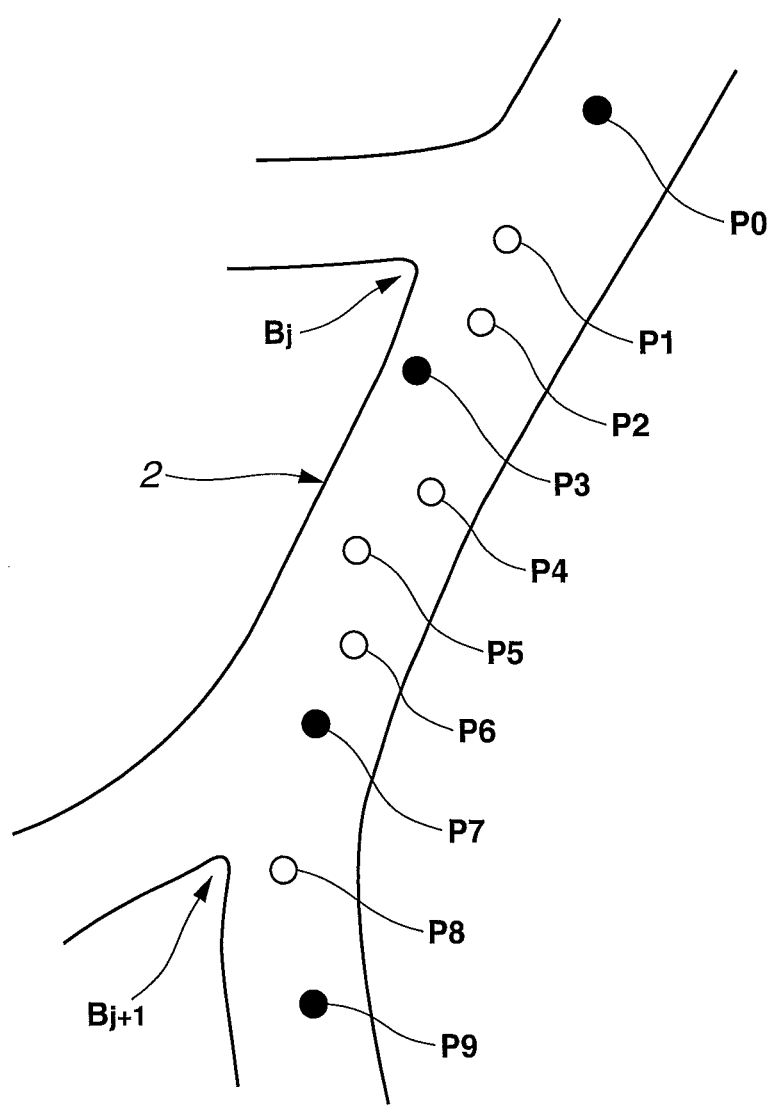
FIG. 14 is a diagram showing respective positions of the image pickup unit and so forth in a case where an operation of acquiring measurement information is continued from a state of FIG. 13.

Then, if a difference between the distance P3Bpj+1 and the distance P2Bpj+1 is not less than the threshold value, the position P3 is displayed in the restart screen. By continuing the processing in the same manner, a state as shown in FIG. 14 is obtained. The positions P4, P5, P6 and P8 indicated by the white circles (in addition to the position P1 shown in FIG. 13) are positions at which the position estimation has succeeded (however, a variation value of the measurement information is within the threshold value), the positions P3, P7 and P9 indicated by the black circles are positions at which the position estimation has succeeded and the measurement information has changed by a value not less than the threshold value, i.e. the positions to be displayed in the restart screen.

Eighth Modified Example

It may be configured that at least two of the first to seventh modified examples are combined.

Ninth Modified Example

Further, in the above-described embodiments, it is described that the associated image generating section 25b generates the associated image in which the bronchia shape image in the three-dimensional shape of the bronchia 2 and the VBS images are combined and the monitor 26 displays the associated image.

By contrast, it may be configured that the associated image generating section 25b generates an associated image in which the position information of the image pickup unit 16 and the tomographic images (MPR images) including the bronchia 2 are synthesized, and the generated associated image is displayed on the monitor 26.

Figure 15:
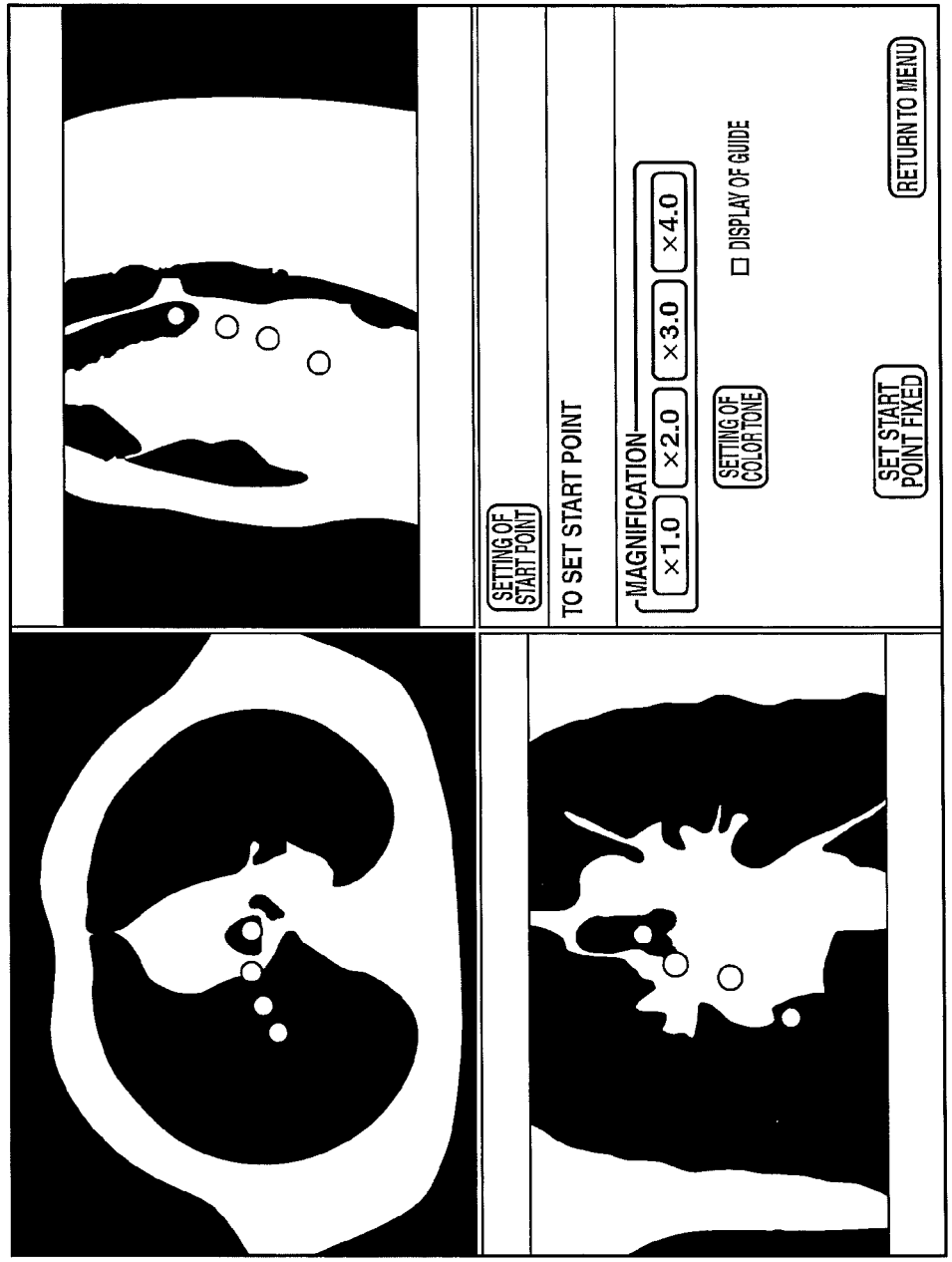
FIG. 15 is a diagram showing display examples of an associated image in a case where the position of the image pickup unit is displayed on a CT tomographic image in a ninth modified example of the second embodiment.

FIG. 15 shows the associated images displayed on the monitor in the present modified example. The upper-left area in FIG. 15 shows a CT tomographic image in transverse section including patient's bronchia, the upper-right area in FIG. 15 shows a CT tomographic image in longitudinal section parallel to a direction of facing the patient's front, the lower-left area in FIG. 15 shows a CT tomographic image in longitudinal section perpendicular to the direction of facing the patient's front, and the lower-right area in FIG. 15 shows a menu screen for setting coordinates by the surgeon.

As shown in FIG. 15, in the present modified example, the position (point) obtained by position measurement by the image pickup unit 16 is displayed by a circle or other shapes of the same color on the tomographic image. In FIG. 15, four positions are displayed in a color (e.g. blue) different from a display color of the tomographic image.

Figure 16:
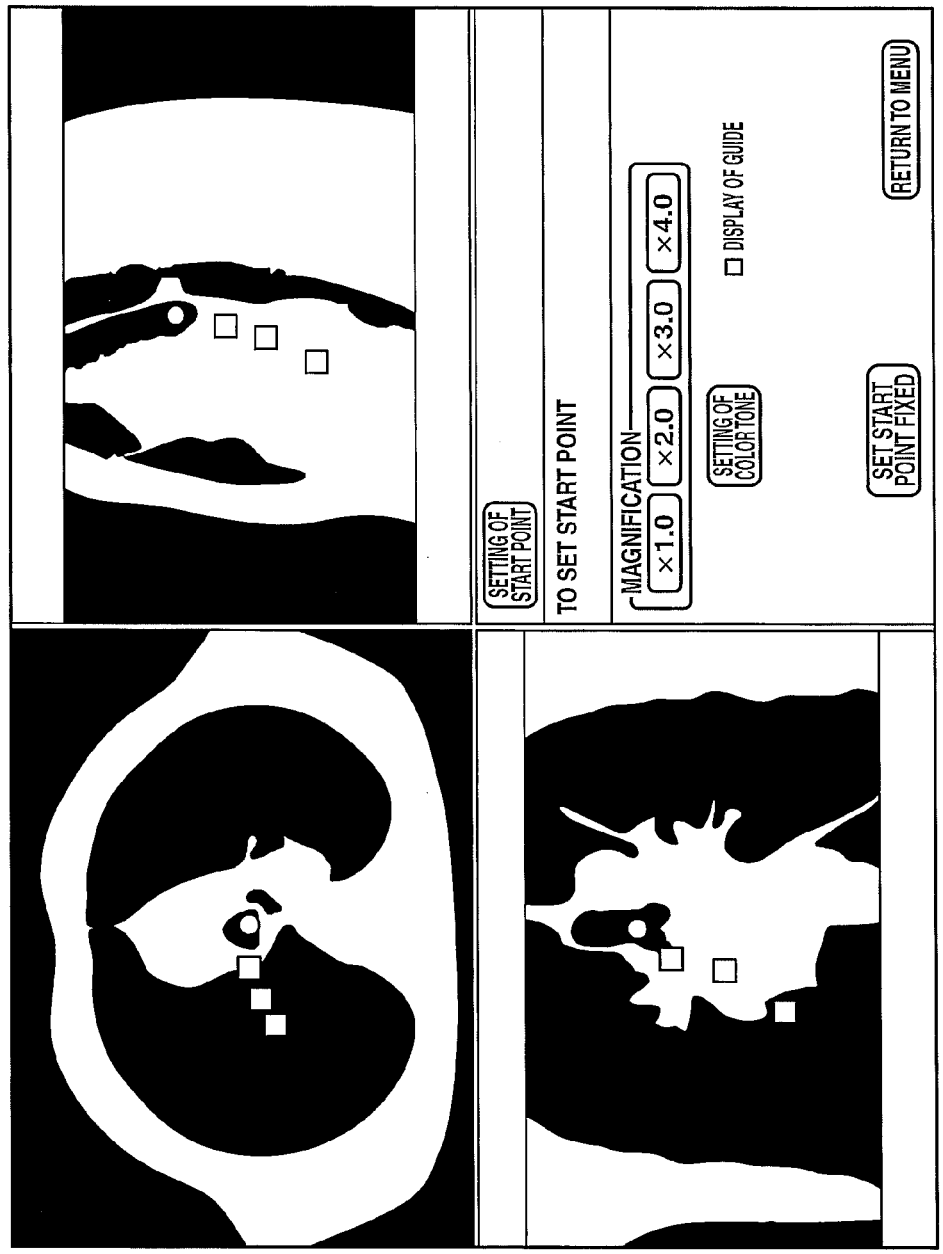
FIG. 16 a diagram showing display examples of displaying the position of the image pickup unit in different shapes for the cases where the position of the image pickup unit is on the section and not on the section.

Further, in FIG. 15, the positions obtained by position measurement are displayed in the same color and the same shape for the cases of being present on the section and the other cases, but as shown in FIG. 16, they may be displayed in different shapes for the case of being present on the section and for the case of not being present on the section (for example, the former by circles and the latter by rectangles), or (in different colors). Further, only the positions on the section may be displayed.

Tenth Modified Example

In the ninth modified example, the case of generating the associated image in which the positions obtained by position measurement by the image pickup unit 16 are displayed on the tomographic image is described, but it may be configured that the tomographic image and the VBS image as the virtual endoscopic image are displayed in combination.

In FIG. 17, it is configured that the positions obtained by position measurement by the image pickup unit 16 are displayed on the tomographic image and the VBS images at the respective positions are displayed, in the case of the ninth modified example as shown in FIG. 15.

Further, in FIG. 17, character information is used for indication such that association of the VBS images with the positions of the image pickup unit 16 can be recognized on the tomographic image. Since four points indicative of the positions of the image pickup unit 16 are shown in FIG. 17, four characters are used for the indication.

Besides, the association of the positions of the image pickup unit 16 with the respective VBS images may be indicated by connection using lines or the like as shown in FIG. 2B.

Further, in the example of FIG. 17, the case of displaying the associated VBS images for all of the positions of the image pickup unit 16, but the VBS images may be displayed for only the positions which are selected on the tomographic image by the surgeon.

Furthermore, it may be configured that the associated VBS images are displayed for all of the positions of the image pickup unit 16 and only the positions associated with the VBS images which are selected by the surgeon are displayed.

Moreover, cases in which different embodiments are configured by partially combining the foregoing embodiments (including modified examples) and so forth belong to the present invention.

What is claimed is:

1. A medical apparatus comprising:
    a storage device configured to store three-dimensional image information of a subject, the three-dimensional image information being acquired in advance;
    an image pickup device configured to acquire an optical image inside the subject; and
    a processor comprising hardware, wherein the processor is configured to implement:
        a luminal organ extracting section configured to extract image information of a three-dimensional shape of a specific luminal organ in the subject from the three-dimensional image information;
        a position correspondence control section configured to generate position correspondence information in an initialization state in which correspondence is set between position information of a predetermined position in the specific luminal organ in a first coordinate system and position information of a distal end portion that is set to the predetermined position in a second coordinate system, thereby setting correspondence between position information in the image information of the three-dimensional shape of the specific luminal organ in the first coordinate system and position information of the image pickup device in the second coordinate system;
        a feature information acquisition section configured to acquire, as feature information, position information related to a branch region where a lumen branches in the image information of the three-dimensional shape of the specific luminal organ extracted by the luminal organ extracting section in a region where the image pickup device is inserted based on the position information of the image pickup device inserted into the specific luminal organ in the first coordinate system, the position information of the image pickup device being caused to have correspondence by the position correspondence control section based on the position information of the image pickup device in the second coordinate system;
        an associated image generating section configured to generate an image in which the position information related to the branch region where the lumen branches is associated with the image information of the three-dimensional shape of the specific luminal organ by superposedly displaying the position information related to the branch region where the lumen branches on the image information of the three-dimensional shape of the specific luminal organ;
        a determination section configured to determine whether the position information of the image pickup device in the first coordinate system, which is caused to have correspondence by the position correspondence control section based on the position information of the image pickup device in the second coordinate system, indicates the image pickup device in the first coordinate system is positioned inside or outside the specific luminal organ in the image information of the three-dimensional shape in the first coordinate system; and
        a control section configured to perform control to display, on a display, a piece of the position information related to the branch region where the lumen branches in a vicinity of the position information of the image pickup device in the specific luminal organ when the determination section determines that the position information of the image pickup device in the first coordinate system is positioned outside of the specific luminal organ, wherein, when the determination section determines that the image pickup device in the first coordinate system is positioned outside the specific luminal organ, the control section corrects the position correspondence information on the basis of a reference position set in the vicinity of the position information of the image pickup device.

2. The medical apparatus according to claim 1, wherein the feature information acquisition section is configured to acquire two-dimensional image information regarding a branch in the specific luminal organ, or is configured to acquire one of pieces of measurement information of: the position of the image pickup device in the specific luminal organ, an inner diameter of the specific luminal organ in a vicinity of the position of the image pickup device, and a distance from the position of the image pickup device to a predetermined position in the specific luminal organ.

3. The medical apparatus according to claim 1, wherein the associated image generating section is configured to generate a branch image of the specific luminal organ in a vicinity of the position information of the image pickup device in the specific luminal organ as the associated image.

4. The medical apparatus according to claim 1, further comprising a position information generating device configured to generate position information on a position where the image pickup device inserted into the specific luminal organ is located.

5. The medical apparatus according to claim 4, wherein the position information generating device comprises a position sensor provided in a vicinity of the image pickup device.

6. The medical apparatus according to claim 1, wherein the display displays the position information related to the branch region where the lumen branches in the vicinity of the position information of the image pickup device in the specific luminal organ, when the determination section determines that the position information of the image pickup device in the first coordinate system is positioned inside the specific luminal organ in the image information of the three-dimensional shape in the first coordinate system.

7. The medical apparatus according to claim 1, further comprising a correspondence information storage device configured to store the position correspondence information.

8. The medical apparatus according to claim 1, wherein, when the determination section makes a first determination that the position information of the image pickup device in the first coordinate system is not positioned inside the specific luminal organ, the control section further controls the display to display a first piece of feature information as the position information related to the branch region where the lumen branches so as to include a position, for a distance from the image pickup device which falls within the first determination, which fulfills a predetermined condition as a position for setting correspondence between the position information of the luminal organ and the position information of the image pickup device within a predetermined distance.

9. The medical apparatus according to claim 8, further comprising an instruction input device configured to perform a correspondence setting instruction for setting correspondence between the position information of the luminal organ in the first coordinate system and the position information of the image pickup device in the second coordinate system at the position where the predetermined condition is fulfilled, wherein the control section is configured to perform control to generate the position correspondence information based on the correspondence setting instruction.

10. The medical apparatus according to claim 1, further comprising an information storage device configured to store the position information of the image pickup device inserted into the specific luminal organ and a picked-up image picked up by the image pickup device in time series.

11. The medical apparatus according to claim 1, wherein, when the determination section determines that the image pickup device is not positioned inside the specific luminal organ, the control section is configured to compare pieces of the position information related to the branch region where the lumen branches in the vicinity of the position of the image pickup device in the first coordinate system with a feature amount calculated from an image picked up by the image pickup device, and to display the position information related to the branch region where the lumen branches which satisfies a predetermined condition.

12. The medical apparatus according to claim 1, further comprising an instruction signal outputting device that outputs an instruction signal in accordance with an input instruction from a user, wherein the control section sets the reference position in the vicinity of the position information of the image pickup device on the basis of the instruction signal outputted by the instruction signal outputting device.

13. The medical apparatus according to claim 1, wherein the feature information acquisition section comprises a measurement processing section configured to acquire measurement information comprising two-dimensional image information related to a branch in the specific luminal organ, a position of the image pickup device in the specific luminal organ, an inner diameter of the specific luminal organ in the vicinity of the position of the image pickup device, and a distance from the position of the image pickup device to the specific position of the specific luminal organ, wherein the medical apparatus further comprises a region setting device that is set so as to separate the specific luminal organ into a plurality of regions along a direction in which a distal end portion of the image pickup device is to be inserted, and wherein the measurement processing apparatus is configured to acquire the position of the image pickup device as the measurement information, the inner diameter of the specific luminal organ, and the distance, while switching the position, the inner diameter, and the distance, for each of the regions set by the region setting device.

* * * * *